United States Patent
Arai et al.

(10) Patent No.: US 11,142,801 B2
(45) Date of Patent: Oct. 12, 2021

(54) TUMOR DETERMINATION METHOD

(71) Applicants: JAPANESE FOUNDATION FOR CANCER RESEARCH, Koto-ku (JP); SEKISUI MEDICAL CO., LTD., Chuo-ku (JP)

(72) Inventors: Masami Arai, Koto-ku (JP); Sachio Nomura, Koto-ku (JP); Yuriko Nemoto, Inzai (JP); Takuya Yotani, Ryugasaki (JP)

(73) Assignees: JAPANESE FOUNDATION FOR CANCER RESEARCH, Koto-ku (JP); SEKISUI MEDICAL CO., LTD., Chuo-ku (JP)

( * ) Notice: Subject to any disclaimer, the term of this patent is extended or adjusted under 35 U.S.C. 154(b) by 345 days.

(21) Appl. No.: 15/766,631

(22) PCT Filed: Oct. 7, 2016

(86) PCT No.: PCT/JP2016/079969
§ 371 (c)(1),
(2) Date: Apr. 6, 2018

(87) PCT Pub. No.: WO2017/061609
PCT Pub. Date: Apr. 13, 2017

(65) Prior Publication Data
US 2019/0062840 A1  Feb. 28, 2019

(30) Foreign Application Priority Data
Oct. 7, 2015 (JP) ............................. JP2015-199819

(51) Int. Cl.
*C12P 19/34* (2006.01)
*C12Q 1/6886* (2018.01)
*G01N 30/88* (2006.01)
*G01N 30/02* (2006.01)
*C12Q 1/68* (2018.01)
*C12N 15/09* (2006.01)
*C12N 15/00* (2006.01)
*C12Q 1/6806* (2018.01)
*B01J 20/281* (2006.01)

(52) U.S. Cl.
CPC ........... *C12Q 1/6886* (2013.01); *C12N 15/00* (2013.01); *C12N 15/09* (2013.01); *C12Q 1/68* (2013.01); *C12Q 1/6806* (2013.01); *G01N 30/02* (2013.01); *G01N 30/48* (2013.01); *G01N 30/88* (2013.01); *C12Q 2600/154* (2013.01)

(58) Field of Classification Search
None
See application file for complete search history.

(56) References Cited

U.S. PATENT DOCUMENTS

| 5,786,146 | A | 7/1998 | Herman et al. | |
| 10,190,172 | B2* | 1/2019 | Kanai | C12Q 1/6886 |
| 2003/0068620 | A1* | 4/2003 | Markowitz | C12Q 1/6886 435/6.14 |
| 2012/0238463 | A1* | 9/2012 | Goel | C12Q 1/6886 506/9 |
| 2014/0242583 | A1* | 8/2014 | Lu | C12Q 1/6886 435/6.11 |
| 2015/0118681 | A1 | 4/2015 | Kanai et al. | |
| 2016/0138097 | A1* | 5/2016 | Yotani | C12Q 1/686 435/6.11 |
| 2017/0058355 | A1 | 3/2017 | Kana et al. | |

FOREIGN PATENT DOCUMENTS

WO  WO 2014/136930 A1  9/2014
WO  WO 2015/129916 A1  9/2015

OTHER PUBLICATIONS

Database accession # BAT 14533 (Year: 2013).*
Database accession # BAT 14534 (Year: 2013).*
Extended European Search Report dated Feb. 26, 2019 in Patent Application No. 16853760.3, 8 pages.
Bettstetter, M. et al. "Distinction of Hereditary Nonpolyposis Colorectal Cancer and Sporadic Microsatellite-Unstable Colorectal Cancer through Quantification of MLH1 Methylation by Real-time PCR" Clinical Cancer Research, vol. 13, NR. 11, XP002788851, 2007, pp. 3221-3228 and Cover Page.
Dinjens, W.N.M. et al. "Guidelines on genetic evaluation and management of Lynch syndrome" Gastrointestinal Endoscopy, vol. 81, No. 1, XP029117165, 2014, pp. 243-244.
Kuismanen, S.A. et al. "Genetic and Epigenetic Modification of MLH1 Accounts for a Major Share of Microsatellite-Unstable Colorectal Cancers" American Journal of Pathology, vol. 156, No. 5, XP003016347, 2000, pp. 1773-1779.

(Continued)

*Primary Examiner* — Kenneth R Horlick
(74) *Attorney, Agent, or Firm* — Oblon, McClelland, Maier & Neustadt, L.L.P.

(57) ABSTRACT

It is intended to provide a method for determining a tumor. The method for determining a tumor comprises: (1) treating genomic DNA prepared from a subject tissue or cell with bisulfite (the subject tissue or cell is derived from a patient who is affected by a tumor and is determined as (i) having MSI-H of the tumor in MSI examination and/or no or reduced expression of MLH1 in the tumor in immunohistochemical examination, and (ii) having no mutation in MLH1 in genetic examination); 2) amplifying, by PCR, DNA comprising a portion or the whole of MLH1 promoter region from the bisulfite-treated DNA; 3) subjecting the PCR amplification product to ion exchange chromatography to obtain a detection signal; 4) determining whether or not the peak of the detection signal is a peak indicating highly methylated DNA; and 5) determining the tumor as a tumor derived from a patient without Lynch syndrome when the peak is determined as a peak indicating highly methylated DNA.

13 Claims, 5 Drawing Sheets

Specification includes a Sequence Listing.

(56) References Cited

OTHER PUBLICATIONS

Cunningham, J.M. et al. "Hypermethylation of the hMLH1 Promoter in Colon Cancer with Microsatellite Instability" Cancer Research, vol. 58, NR. 15, XP002788852, 1998, pp. 3455-3460.
International Search Report dated Jan. 10, 2017 in PCT/JP2016/079969, 2 pages.
Kane, M.F. et al., "Methylation of the hMLH1 Promoter Correlates with Lack of Expression of hMLH1 in Sporadic Colon Tumors and Mismatch Repair-defective Human Tumor Cell Lines[1]", Cancer Research, vol. 57, (1997), pp. 808-811.
Issa, J-P, "CpG island methylator phenotype in cancer" Perspectives, vol. 4, (2004), pp. 988-993.
Toyota, M. et al., "CpG island methylator phenotype in colorectal cancer", Proc. Natl. Acad. Sci., vol. 96, (1999), pp. 8681-8686.
Shen, L. et al., "Integrated genetic and epigenetic analysis identifies three different subclasses of colon cancer", PNAS, vol. 104, No. 47, (2007), pp. 18654-18659, with Supplemental Data (11 Sheets).
Toyota, M. et al., Aberrant Methylation in Gastric Cancer Associated with the CpG Island Methylator Phenotype[1], Cancer Research, vol. 59, (1999), pp. 5438-5442.
Herman, J.G. et al., "Methylation-specific PCR: A novel PCR assay for methylation status of CpG islands", Proc. Natl. Acad. Sci., vol. 93, (1996), pp. 9821-9826.
Sadri, R. et al., "Rapid analysis of DNA methylation using new restriction enzyme sites created by bisulfite modification", Nucleic Acids Research, vol. 24, No. 24, (1996), pp. 5058-5059.
Xiong, Z. et al., "COBRA: a sensitive and quantitative DNA methylation assay", Nucleic Acids Research, vol. 25, No. 12, (1997), pp. 2532-2534.
Ronaghi, M. et al., "A Sequencing Method Based on Real-Time Pyrophisphate", Science, vol. 281, (1998), pp. 363-365.
Ronaghi, M., "Pyrosequencing Sheds Light on DNA Sequencing", Genome Research, vol. 3, (2001), pp. 3-11.
Announcements in Ministry of Health, Labour and Welfare, and Revision of Medical Fee on Apr. 2008, (2007), 5 pages.
Vilar, E. et al., "Microsatellite instability in colorectal cancer—the stable evidence", Nat. Rev. Clin. Oncol., vol. 7, No. 3, (2010), 22 pages.
Ishikubo, T. et al., "The clinical features of rectal cancers with high-frequency microsatellite instability (MSI-H) in Japanese males", Science Direct, Cancer Letter No. 216, (2004), pp. 55-62.
Asaka, S-i et al., Microsatellite instability-low colorectal cancer acquires a KRAS mutation during the progression from Dukes' A to Dukes' B, Carcinogenesis, vol. 30, No. 30, (2009), pp. 494-499.
Umar, A. et al., "Revised Bethesda Guidelines for Hereditary Nonpolyposis Colorectal Caner (Lynch Syndrome) and Microsatellite Instabiity", J. Natl. Cancer Inst., vol. 96, No. 4, (2004), 16 pages.
Vasen, H. F.A. et al., "Revised guidelines for the clinical management of Lynch syndrome (HNPCC): recommendations by a group of European experts", Gut, vol. 62, (2013), pp. 812-823.
Uhlmann, K. et al., "Evaluation of a potential epigenetic biomarker by quantitative methy-single nucleotide polymorphism analysis", Electrophoresis, vol. 23, (2002), pp. 4072-4079.
Chinese Office Action issued in corresponding Chinese Application No. 201680059152.6 dated Sep. 22, 2020.with English Translation.
Lars Henrik Jensen, et al., "Regulation of MLH1 mRNA and protein expression by promoter methylation in primary colorectal cancer: a descriptive and prognostic cancer marker study", Cell Oncol. (2013) 36:411-419.

\* cited by examiner

[Figure 1]
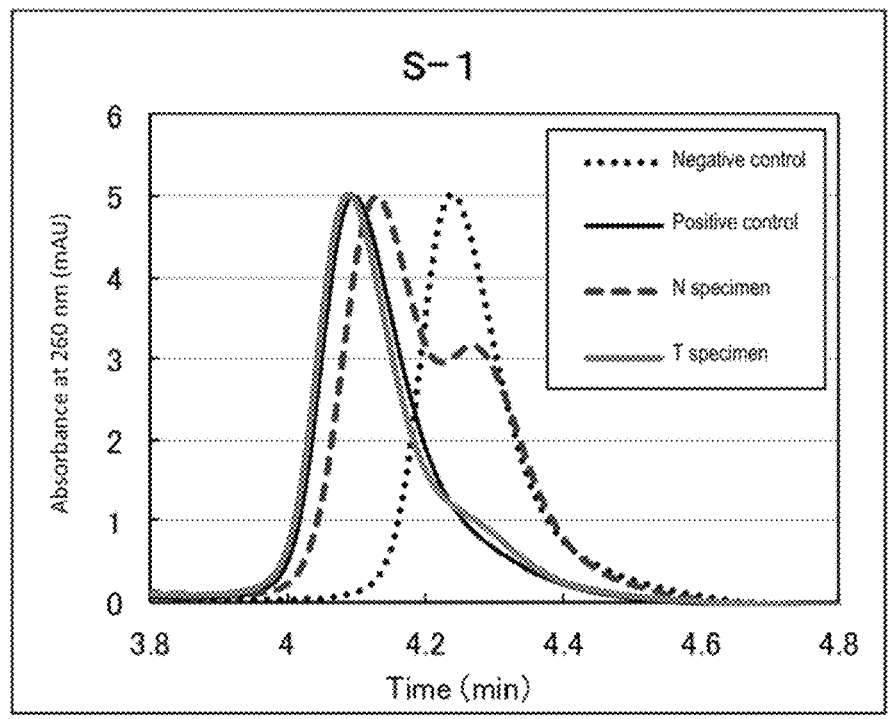
[Figure 2]
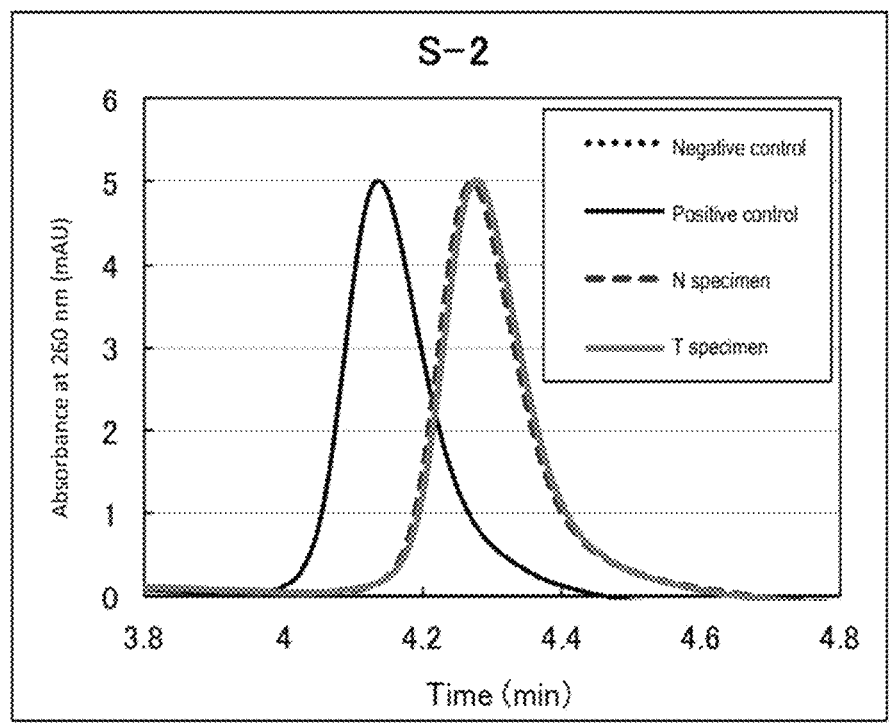

[Figure 3]
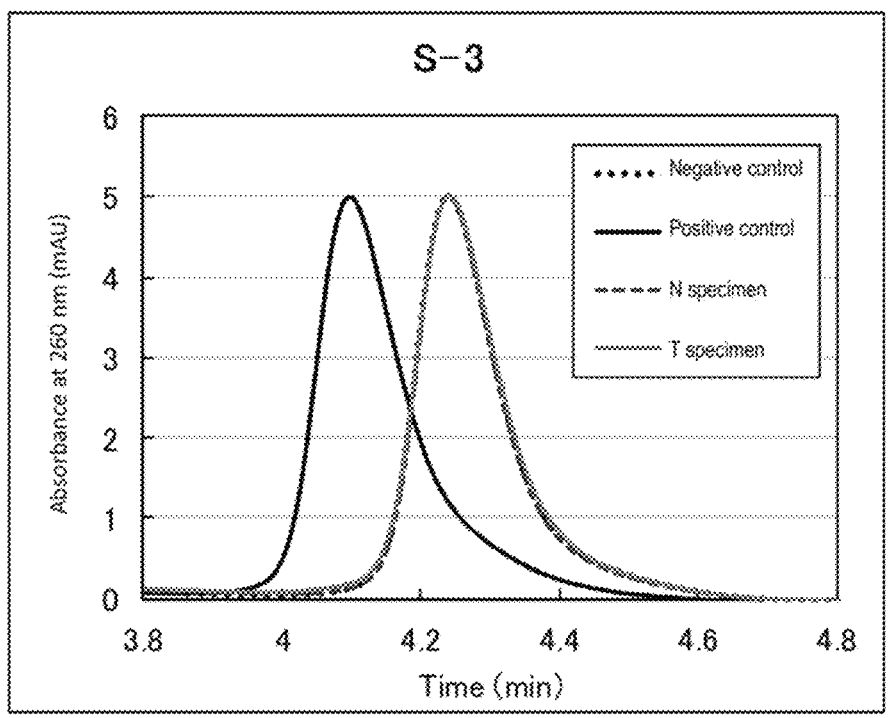
[Figure 4]
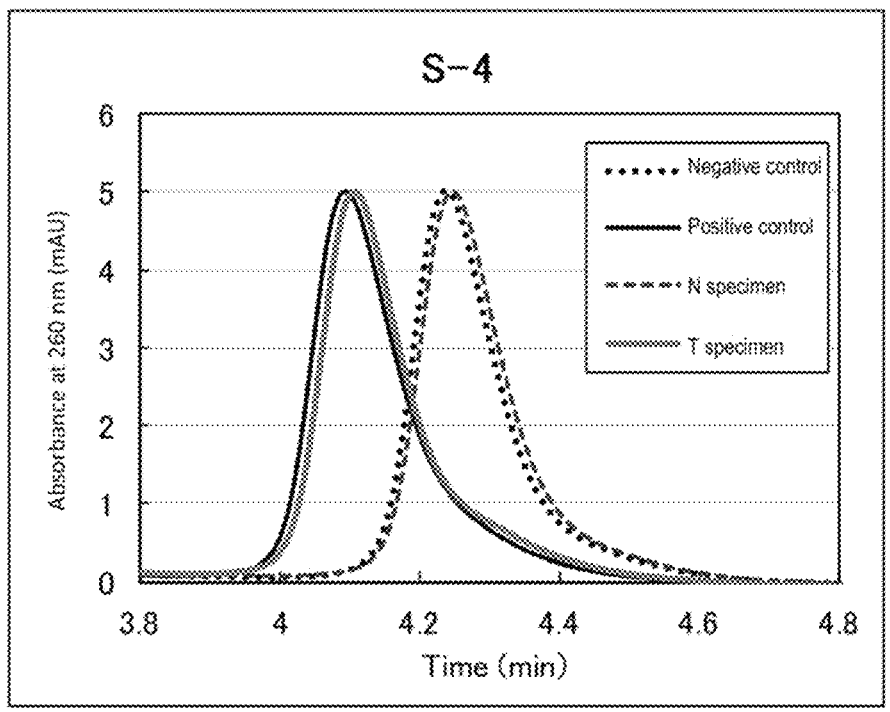

[Figure 5]
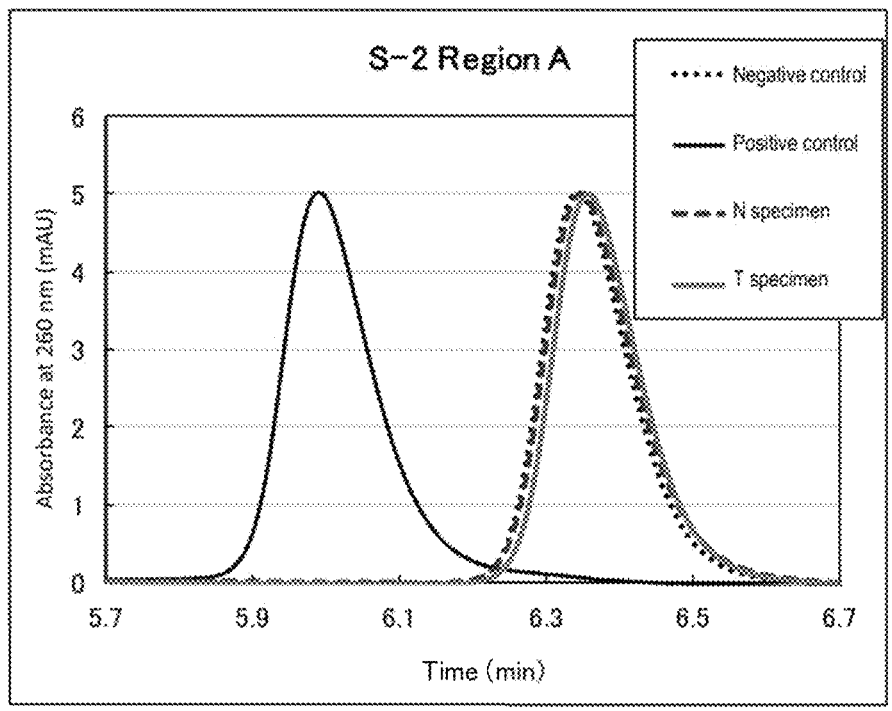
[Figure 6]
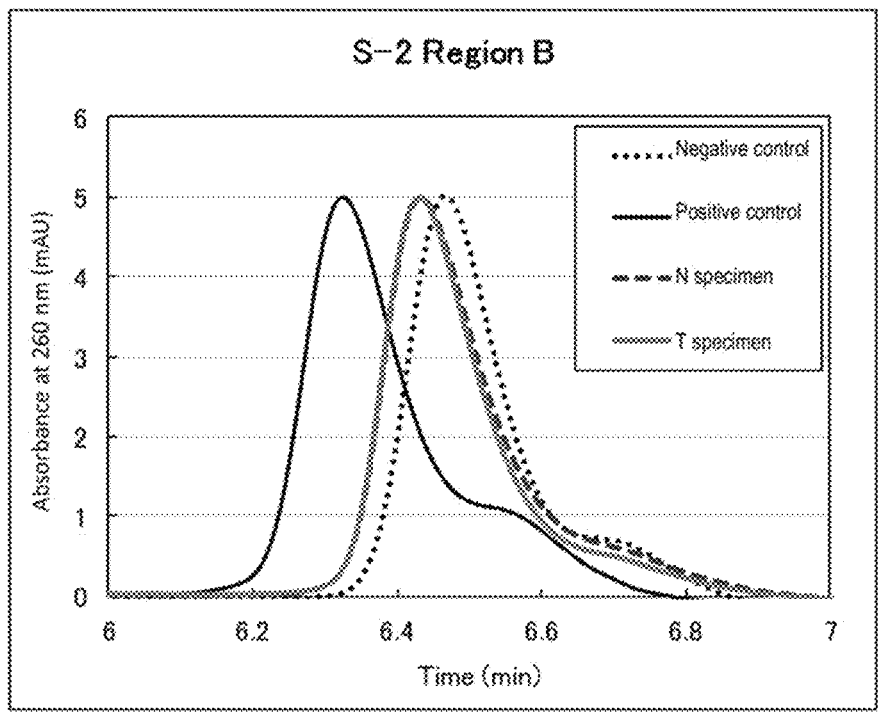

[Figure 7]
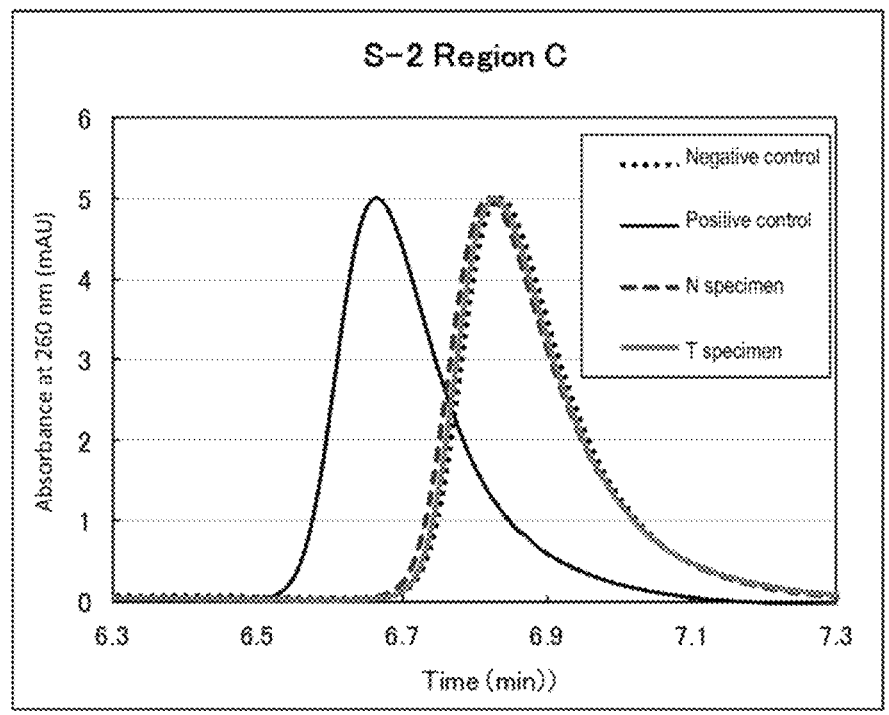
[Figure 8]
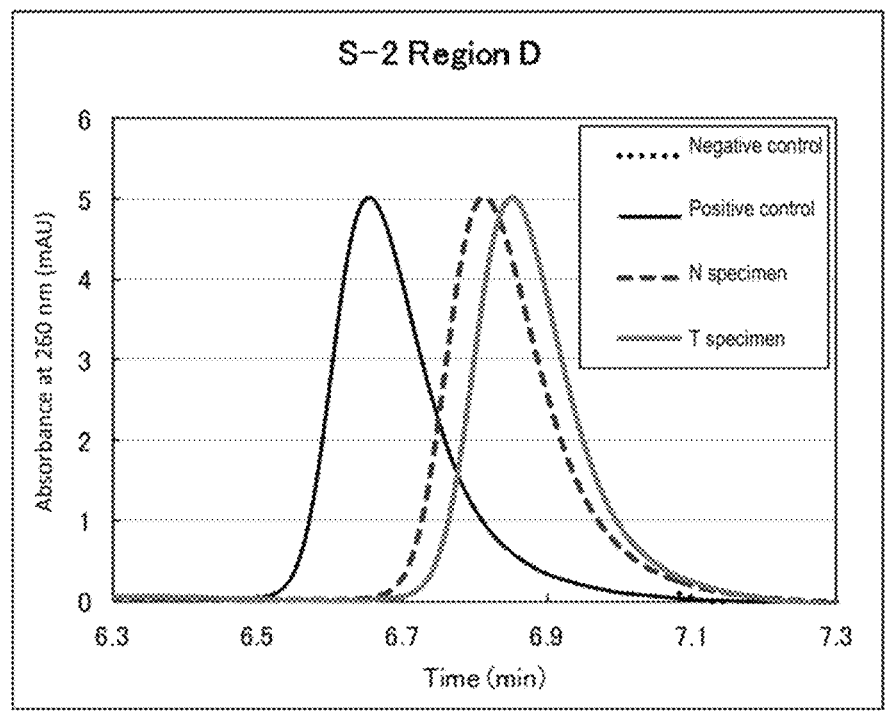

[Figure 9]
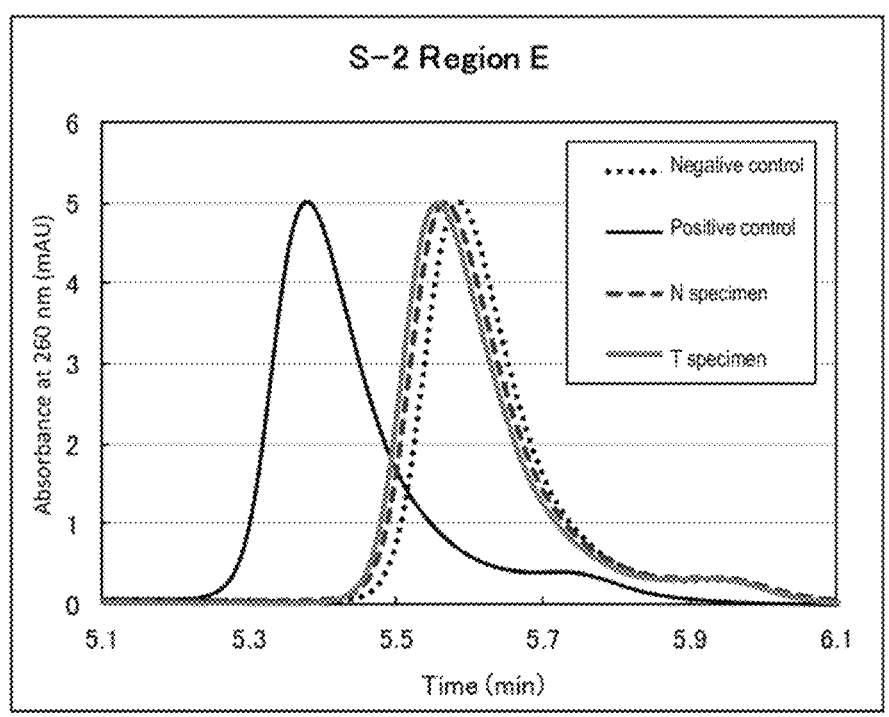

TUMOR DETERMINATION METHOD

FIELD OF THE INVENTION

The present invention relates to a method for determining a tumor by use of the detection of methylated DNA by ion exchange chromatography.

BACKGROUND OF THE INVENTION

In recent years, abnormal methylation of DNA has been found to be deeply involved in malignant transformation and has received attention. Abnormal DNA methylation of CpG islands in some gene promoter regions is known as a characteristic epigenetic abnormality in tumors. The CpG island is a region in which a two-nucleotide sequence of cytosine (C)-guanine (G) via a phosphodiester bond (p) appears with high frequency. This region often resides in a promoter region upstream of a gene. The abnormal DNA methylation of the CpG island is involved in carcinogenesis through the inactivation of tumor suppressor genes, etc. DNA hypermethylation of the CpG island correlating with clinicopathological factors has been reported in colorectal cancer, stomach cancer, etc. (Non Patent Literatures 1 to 4).

Already established methods for analyzing methylated DNA include a method based on bisulfite reaction. This method is a method most generally used in the analysis of methylated DNA. The treatment of single-stranded DNA with bisulfite converts cytosine to uracil through sulfonation, hydrolic deamination, and desulfonation. On the other hand, methylated cytosine is left unaltered throughout the reaction time of actually performed bisulfite treatment because the reaction rate of sulfonation as the first step is very slow. Thus, PCR (polymerase chain reaction) using the bisulfite-treated DNA amplifies unmethylated cytosine with the uracil replaced with thymine, while leaving the methylated cytosine unaltered. The methylation status is analyzed through the use of the difference between the bases cytosine and thymine appearing in the sequence of this PCR amplification product. Methods generally used according to this basic principle are methylation-specific PCR (MSP) described in Patent Literature 1 and Non Patent Literature 5, and combined bisulfite restriction analysis (COBRA) described in Non Patent Literatures 6 and 7. The MSP method and the COBRA method are methylated DNA analysis methods currently used widely because these methods are capable of quantitatively analyzing methylated DNA without special equipment. A problem of the methods, however, is time and labor required for electrophoresis used in the analysis and additional restriction enzyme treatment necessary for the COBRA method.

An alternative methylated DNA analysis method is pyrosequencing (Non Patent Literatures 8 and 9). This method involves subjecting a PCR amplification product of bisulfite-treated DNA to pyrosequencing, and detecting methylated cytosine replaced for thymine. However, the pyrosequencing requires a dedicated sequencer and also requires time-consuming analysis because of reading bases one by one, and expensive reagents.

Recently, a method for determining a DNA methylation rate, comprising subjecting a PCR amplification product of bisulfite-treated DNA to ion exchange chromatography, and determining the DNA methylation rate on the basis of the retention time of a detection signal of the chromatography has been proposed (Patent Literature 2). This method has the advantage that the analysis time is drastically shortened as compared with the conventional methylated DNA analysis methods using electrophoresis or pyrosequencing. Also, a method for determining the prognosis of renal cell carcinoma by use of the method of Patent Literature 2 has been proposed (Patent Literature 3).

Hereditary non-polyposis colorectal cancer (HNPCC), one type of hereditary colorectal cancer, is also called Lynch syndrome. This cancer develops at an earlier age as compared with general colorectal cancer, while occurring multiply (synchronously or metachronously) and appearing more commonly in the right side colon. HNPCC has a higher frequency of poorly differentiated adenocarcinoma than that of sporadic colorectal cancer and exhibits histological features such as mucinous carcinoma- or signet ring cell-like differentiation and intratumoral lymphocyte infiltration. The colorectal cancer caused by Lynch syndrome is handled with nonhereditary sporadic colorectal cancer without distinction due to its poor clinical feature, and is reportedly likely to be left undiagnosed in most cases. Since Lynch syndrome patients have a high risk of developing various malignant tumors other than colorectal cancer, such as gynecological cancer and digestive system cancer, the diagnosis of Lynch syndrome is important. Microsatellite instability (MSI) examination and mismatch repair (MMR)-associated protein immunohistochemistry are usefully used as screening examination for the diagnosis of Lynch syndrome, and the former is already covered by insurance (Non Patent Literature 10).

A microsatellite, a region of DNA in which a nucleotide sequence of one to several bases appears repetitively, is susceptible to DNA replication errors. Microsatellite instability (MSI) means that the number of repeats of microsatellites varies between tumor tissues and normal tissues due to decline in the functions of the mismatch repair mechanism. MSI is found in approximately 90% of colorectal cancer tissues diagnosed with Lynch syndrome.

MSI is classified into MSS (stable), MSI-L (low), and MSI-H (high) on the basis of the instability of repeat sequences detected by 5 types of microsatellite markers: BAT25, BAT26, D2S123, D5S346, and D17S250. (Non Patent Literature 11). More specifically, MSI positivity (MSI high: MSI-H) means that MSI is found by at least two of these microsattelite markers. The case where MSI is found by one tumor marker is called MSI negativity (MSI low: MSI-L). The case where MSI negativity is determined as to all the 5 types of markers is called microsatellite stable (MSS). Alternatively, MSI examination may be conducted using 6 or more markers including the 5 types of markers. In such a case, MSI-H is determined when MSI is found in 30 to 40% or more of all the markers, and MSI-L is determined when MSI is found below this level. MSI is known to be caused by a mutation in the germline of a mismatch repair gene MLH1, MSH2, MSH6, or PMS2.

Colorectal cancer with MSI-H is reportedly 6 to 7% of all colorectal cancer cases in Japan (Non Patent Literatures 12 and 13). On the other hand, Lynch syndrome patients are reportedly 2 to 3% of all colorectal cancer patients. Thus, ½ to ⅔ of the MSI-H cases have no Lynch syndrome and are considered to involve inactivation due to the acquired methylation of MLH1 promoter region (Non Patent Literature 14). The Bethesda Guidelines have been established in order to exclude such a methylation case from patients suspected of having Lynch syndrome (Non Patent Literature 15). A case which satisfies the guidelines seems to be efficiently applied to MSI examination. Meanwhile, it has been pointed out that the Bethesda Guidelines overlook Lynch syndrome of low penetrance which develops at age fifty-something. Recently, it has also been pointed out that immunohistochemistry or MSI examination is conducted on all colorectal cancer cases (or colorectal cancer in patients under the age 70) to pick up Lynch syndrome (Non Patent Literature 16). Genetic examination may be preceded according to past medical history or family history, particularly, for a MSI-H case immunohistochemically confirmed to have the disappearance of MLH1 expression.

CITATION LIST

Patent Literature

[Patent Literature 1] U.S. Pat. No. 5,786,146
[Patent Literature 2] WO 2014/136930
[Patent Literature 3] WO 2015/129916

Non Patent Literature

[Non Patent Literature 1] Nat. Rev. Cancer, 4, 988-993 (2004)
[Non Patent Literature 2] Proc. Natl. Acad. Sci. USA, 96, 8681-8686 (1999)
[Non Patent Literature 3] Proc. Natl. Acad. Sci. USA, 104, 18654-18659 (2007)
[Non Patent Literature 4] Cancer Res., 59, 5438-5442 (1999)
[Non Patent Literature 5] Proc. Natl. Acad. Sci. USA, 93, 9821-9826 (1996)
[Non Patent Literature 6] Nucleic Acids Res., 24, 5058-5059 (1996)
[Non Patent Literature 7] Nucleic Acids Res., 25, 2532-2534 (1997)
[Non Patent Literature 8] Science, 281, 363-365(1998)
[Non Patent Literature 9] Genome Research, 11, 3-11(2001)
[Non Patent Literature 10] Jun. 1, 2007, Announcements in Ministry of Health, Labour and Welfare, and Revision of Medical Fee on April, 2008
[Non Patent Literature 11] Nat. Rev. Clin. Oncol., 7, 153-162(2010)
[Non Patent Literature 12] Cancer Lett., 216, 55-62(2004)
[Non Patent Literature 13] Carcinogenesis, 30, 494-499 (2009)
[Non Patent Literature 14] Cancer Res., 57, 808-811(1997)
[Non Patent Literature 15] J. Natl. Cancer Inst., 96, 261-268(2004)
[Non Patent Literature 16] Gut., 62, 812-823(2013)
[Non Patent Literature 17] Electrophoresis, 23, 4072-4079 (2002)

SUMMARY OF THE INVENTION

Problem to be Solved by the Invention

More accurate colorectal cancer diagnosis requires analyzing the methylation of MLH1 promoter region in a larger number of colorectal cancer cases. The methylation of MLH1 promoter region has been analyzed so far by treating DNA with bisulfite, followed by PCR-direct sequence, MSP, RFLP (restriction fragment length polymorphism by which methylation is recognized), or the like. A methylation screening method using pyrosequencing is exploited in clinical practice (Non Patent Literature 17). However, the pyrosequencing disadvantageously requires cost and time. Thus, there is a demand for the development of a more versatile approach with low cost.

Means for Solving the Invention

The present inventors have found that a signal obtained by subjecting a PCR amplification product of bisulfite-treated DNA to ion exchange chromatography differs between patients with Lynch syndrome and patients without Lynch syndrome having a microsatellite instability-positive (MSI-H) tumor.

Accordingly, the present invention provides the followings:

[1] A method for determining a tumor, comprising:
(1) treating genomic DNA prepared from a subject tissue or cell with bisulfite, wherein
the subject tissue or cell is a tissue or a cell derived from a patient who is affected by a tumor and is determined as
   (i) having MSI-H of the tumor in MSI examination and/or no or reduced expression of MLH1 in, the tumor in immunohistochemical examination, and
   (ii) having no mutation in MLH1 in genetic examination;
(2) amplifying, by PCR, DNA comprising a portion or the whole of MLH1 promoter region from the bisulfite-treated DNA obtained in the step (1);
(3) subjecting the PCR amplification product obtained in the step (2) to ion exchange chromatography to obtain a detection signal;
(4) determining whether or not the peak of the detection signal obtained in the step (3) is a peak indicating highly methylated DNA; and
(5) determining the tumor as a tumor derived from a patient without Lynch syndrome when the peak is determined as a peak indicating highly methylated DNA in the step (4).

[2] The method according to [1], wherein the subject tissue or cell is a tumor-containing tissue or cell.

[3] The method according to [2], wherein the tumor is a tumor in the large intestine, the endometrium, the stomach, the ovarium, the small intestine, the bile duct, the pancreas, the renal pelvis, the urinary duct, the brain, or the sebaceous gland.

[4] The method according to any one of [1] to [3], wherein in the step (2), DNA comprising a portion or the whole of MLH1 promoter region and/or intron 1 region is amplified by PCR instead of the DNA comprising a portion or the whole of MLH1 promoter region.

[5] The method according to any one of [1] to [4], wherein the ion exchange chromatography is anion exchange chromatography.

[6] The method according to any one of [1] to [5], wherein the column packing material for use in the ion exchange chromatography has both a strong cationic group and a weak cationic group on the surface.

Effects of the Invention

The method of the present invention is useful in differential diagnosis for denying the possibility of Lynch syndrome in patients suspected of having Lynch syndrome by conventional MSI examination or the like, but manifesting no abnormality in MLH1 in genetic examination. Furthermore, the method of the present invention can determine the possibility of Lynch syndrome more rapidly, conveniently, and highly accurately. Therefore, the present invention enables selection of an appropriate treatment method for patients. Thus, the present invention contributes to improvement in the survival rate of patients.

BRIEF DESCRIPTION OF THE DRAWINGS

FIG. 1 shows chromatograms of a T specimen and a N specimen from patient ID: 8-1 as to region DfCr, a negative control, and a positive control. The abscissa depicts chromatography retention times.

FIG. 2 shows chromatograms of a T specimen and a N specimen from patient ID: S-2 as to region DfCr, a negative control, and a positive control. The abscissa depicts chromatography retention times.

FIG. 3 shows chromatograms of a T specimen and a N specimen from patient ID: S-3 as to region DfCr, a negative control, and a positive control. The abscissa depicts chromatography retention times.

FIG. 4 shows chromatograms of a T specimen and a N specimen from patient ID: S-4 as to region DfCr, a negative control, and a positive control. The abscissa depicts chromatography retention times.

FIG. 5 shows chromatograms of a T specimen and a N specimen from patient ID: S-2 as to region A, a negative control, and a positive control. The abscissa depicts chromatography retention times.

FIG. 6 shows chromatograms of a T specimen and a N specimen from patient ID: S-2 as to region B, a negative control, and a positive control. The abscissa depicts chromatography retention times.

FIG. 7 shows chromatograms of a T specimen and a N specimen from patient ID: S-2 as to region C, a negative control, and a positive control. The abscissa depicts chromatography retention times.

FIG. 8 shows chromatograms of a T specimen and a N specimen from patient ID: S-2 as to region D, a negative control, and a positive control. The abscissa depicts chromatography retention times.

FIG. 9 shows chromatograms of a T specimen and a N specimen from patient ID: S-2 as to region E, a negative control, and a positive control. The abscissa depicts chromatography retention times.

EMBODIMENTS FOR CARRYING OUT THE INVENTION

In the present specification, the "Lynch syndrome" is an autosomal dominantly inherited disease caused by a mutation in the germline of a mismatch repair gene and means a tumor susceptibility syndrome for Lynch syndrome-associated tumors described below. The "Lynch syndrome" is generally handled as an identical disease to hereditary non-polyposis colorectal cancer (HNPCC), one type of hereditary colorectal cancer. In Lynch syndrome patients, however, tumors may occur in various tissues including tissues of not only the large intestine but the endometrium, the stomach, the ovarium, the small intestine, the bile duct, the pancreas, the renal pelvis the urinary duct, the brain, and the sebaceous gland. These tumors found in Lynch syndrome patients are called Lynch syndrome-associated tumors. The "Lynch syndrome-associated tumor" according to the present invention is not limited to colorectal cancer and encompasses tumors which occur in the aforementioned various tissues found in Lynch syndrome patients.

The "epimutation" is an epigenetic abnormality which brings about usually the transcriptional silencing of an active gene or usually the activation of a silent gene without changing the DNA sequence of an affected gene.

The "constitutional epimutation" is an epimutation which is present in normal cells (provided that the epimutation may be absent in germ cells) of an individual and is responsible for the phenotype of a disease.

The "Germ line epimutation" is an epimutation which is present in a gamete (which has undergone no epigenetic modification) and influences one of the alleles of a parent.

In the present specification, the "tumor" encompasses benign tumors and malignant tumors (cancer).

In the present specification, the "CpG site" means a site where a phosphodiester bond (p) is formed between cytosine (C) and guanine (G) in DNA. In the present specification, the CpG island refers to a region in which a two-nucleotide sequence of cytosine (C)-guanine (G) via a phosphodiester bond (p) appears with high frequency. The CpG island often resides in a promoter region upstream of a gene. In the present specification, the "CpG site or CpG island of (a) gene" means a CpG island located at a position close to the coding region of the gene, or a CpG site contained in the CpG island, and preferably means a CpG site or a CpG island present in the promoter region of the gene. The CpG site or the CpG island of a particular gene can be identified on the basis of a method such as MassARRAY method or pyrosequencing.

In the present specification, the "DNA methylation" means a state where carbon at position 5 of cytosine in DNA is methylated. In the present specification, the phrase "detecting methylation" of DNA means to measure the presence or absence, abundance, or abundance ratio of methylated DNA in this DNA, or the methylation rate of this DNA. In the present specification, the "DNA methylation rate" means the proportion of methylated cytosine of a CpG site in particular DNA to be detected and can be indicated by, for example, the ratio of the number of methylated cytosine to the total number of cytosine (methylated cytosine and unmethylated cytosine) in the CpG site of the particular DNA region to be detected.

In the present specification, the "highly methylated DNA (or also simply referred to as methylated DNA)" means DNA having a methylation rate of, for example, 50% or more, preferably 70% or more, more preferably 90% or more. The "low methylated DNA (or also referred to as unmethylated DNA)" means DNA having a DNA methylation rate of, for example, less than 50%, preferably 20% or less, more preferably 10% or less, further preferably 5% or less. In the present specification, the "peak indicating highly methylated DNA (or also simply referred to as methylated DNA)" means a peak of a chromatography detection signal obtained from the highly methylated DNA. The "peak indicating low methylated DNA (or unmethylated DNA)" means a peak of a chromatography detection signal obtained from the low methylated DNA. The DNA methylation rate can be determined by a method known in the art such as pyrosequencing. In the method of the present invention, the "highly methylated DNA" and the "low methylated DNA" are determined on the basis of a DNA methylation rate calculated from the chromatogram of ion exchange chromatography by procedures mentioned later.

In the present specification, the "retention time" means the time from analyte injection into a column through elution in chromatography such as column chromatography, and in other words, means the time during which the analyte is retained in the column. Retention time is sometimes also referred to as elution time. The retention time (elution time) of a detection signal of ion exchange chromatography correlates to a DNA methylation rate (see Patent Literature 2). Thus, the DNA methylation rate can be calculated by measuring the retention time (elution time) of a detection signal of ion exchange chromatography. More specifically, a calibration curve of retention times of chromatography detection signals is prepared from the DNA of standards having known methylation rates. The methylation rate of sample DNA can be calculated by applying the retention time of the chromatography detection signal of the sample DNA to this calibration curve. In the case of calculating a DNA methylation rate from a chromatogram having a plurality of detection signals (peaks), an average retention time of the detection signals can be first calculated and subsequently converted to an average DNA methylation rate, as disclosed in, for example, Patent Literature 3.

In one embodiment, the present invention provides a method for determining a tumor, comprising:
(1) treating genomic DNA prepared from a subject tissue or cell with bisulfite, wherein
the subject tissue or cell is a tissue or a cell derived from a patient who is affected by a tumor and is determined as
(i) having MSI-H of the tumor in MSI examination and/or no or reduced expression of MLH1 in the tumor in immunohistochemical examination, and
(ii) having no mutation in MLH1 in genetic examination;
(2) amplifying, by PCR, DNA comprising a portion or the whole of MLH1 promoter region from the bisulfite-treated DNA obtained in the step (1);
(3) subjecting the PCR amplification product obtained in the step (2) to ion exchange chromatography to obtain a detection signal;
(4) determining whether or not the peak of the detection signal obtained in the step (3) is a peak indicating highly methylated DNA; and
(5) determining the tumor as a tumor derived from a patient without Lynch syndrome when the peak is determined as a peak indicating highly methylated DNA in the step (4).

In another embodiment, the present invention provides a method for determining a tumor patient, comprising:
(1) treating genomic DNA prepared from a subject tissue or cell with bisulfite, wherein
the subject tissue or cell is a tissue or a cell derived from a patient who is affected by a tumor and is determined as
(i) having MSI-H of the tumor in MSI examination and/or no or reduced expression of MLH1 in the tumor in immunohistochemical examination, and
(ii) having no mutation in MLH1 in genetic examination;
(2) amplifying, by PCR, DNA comprising a portion or the whole of MLH1 promoter region from the bisulfite-treated DNA obtained in the step (1);
(3) subjecting the PCR amplification product obtained in the step (2) to ion exchange chromatography to obtain a detection signal;
(4) determining whether or not the peak of the detection signal obtained in the step (3) is a peak indicating highly methylated DNA; and
(5) determining the patient as a patient without Lynch syndrome when the peak is determined as a peak indicating highly methylated DNA in the step (4).

In an alternative embodiment, the present invention provides a method for measuring methylated DNA for determining a patient without Lynch syndrome from tumor patients, comprising:
(1) treating genomic DNA prepared from a subject tissue or cell with bisulfite, wherein
the subject tissue or cell is a tissue or a cell derived from a patient who is affected by a tumor and is determined as
(i) having MSI-H of the tumor in MSI examination and/or no or reduced expression of MLH1 in the tumor in immunohistochemical examination, and
(ii) having no mutation in MLH1 in genetic examination;
(2) amplifying, by PCR, DNA comprising a portion or the whole of MLH1 promoter region from the bisulfite-treated DNA obtained in the step (1);
(3) subjecting the PCR amplification product obtained in the step (2) to ion exchange chromatography to obtain a detection signal; and
(4) determining whether or not the peak of the detection signal obtained in the step (3) is a peak indicating highly methylated DNA, wherein
the patient is determined as a patient without Lynch syndrome when the peak is determined as a peak indicating highly methylated DNA in the step (4).

In a further alternative embodiment, the present invention provides a method for obtaining data for determining a tumor, comprising:
(1) treating genomic DNA prepared from a subject tissue or cell with bisulfite, wherein
the subject tissue or cell is a tissue or a cell derived from a patient who is affected by a tumor and is determined as
(i) having MSI-H of the tumor in MSI examination and/or no or reduced expression of MLH1 in the tumor in immunohistochemical examination, and
(ii) having no mutation in MLH1 in genetic examination;
(2) amplifying, by PCR, DNA comprising a portion or the whole of MLH1 promoter region from the bisulfite-treated DNA obtained in the step (1);
(3) subjecting the PCR amplification product obtained in the step (2) to ion exchange chromatography to obtain a detection signal; and
(4) obtaining whether or not the peak of the detection signal obtained in the step (3) is a peak indicating highly methylated DNA as data for determining whether or not the tumor is a tumor derived from a patient without Lynch syndrome.

Examples of the subject to which the embodiments of the present invention described above are applied include patients affected by a tumor and desired to confirm that the tumor is not a tumor caused by Lynch syndrome. More specifically, the subject is a patient affected by a tumor and determined as (i) having MSI-H of the tumor in MSI examination and/or no or reduced expression of MLH1 in the tumor in immunohistochemical examination, and (ii) having no mutation in MLH1 in genetic examination. Examples of the tumor include, but are not particularly limited to, tumors in the oral cavity, the tongue, the throat, the esophagus, the stomach, the duodenum, the small intestine, the large intestine, the liver, the pancreas, the gallbladder, the bile duct, the kidney, the renal pelvis, the adrenal grand, the urinary duct, the mammary gland, the prostate, the testis, the ovarium, the uterus, the lung, the brain, the sebaceous gland, the skin, blood, lymph, and the bone marrow and preferably include tumors in the large intestine, the endometrium, the stomach, the ovarium, the small intestine, the bile duct, the pancreas, the renal pelvis, the urinary duct, the brain, and the sebaceous gland. More preferably, the tumor is a tumor of the large intestine.

The subject tissue or cell used in the present embodiment is a tumor-containing tissue or cell derived from the subject and is preferably a tumor-containing tissue or cell in the large intestine, the endometrium, the stomach, the ovarium, the small intestine, the bile duct, the pancreas, the renal pelvis, the urinary duct, the brain, or the sebaceous gland. Alternatively, the subject tissue or cell used in the present embodiment may be a non-tumor tissue or cell derived from the subject. The method of the present embodiment using the non-tumor tissue or cell enables determination of a patient having DNA methylation caused by epimutation.

In an additional embodiment, the present invention provides a method for differentiating between Lynch syndrome-derived and non-Lynch syndrome-derived tissues or cells, comprising:
(1) treating genomic DNA prepared from a subject tissue or cell with bisulfite;

(2) amplifying, by PCR, DNA comprising a portion or the whole of MLH1 promoter region from the bisulfite-treated DNA obtained in the step (1);
(3) subjecting the PCR amplification product obtained in the step (2) to ion exchange chromatography to obtain a detection signal of methylated DNA; and
(4) comparing the peak value of the detection signal of methylated DNA obtained in the step (3) with peak values of a control group to measure a variation.

In an additional embodiment, the present invention provides a method for determining a tissue or a cell, comprising:
(1) treating genomic DNA prepared from a subject tissue or cell with bisulfite;
(2) amplifying, by PCR, DNA comprising a portion or the whole of MLH1 promoter region from the bisulfite-treated DNA obtained in the step (1);
(3) subjecting the PCR amplification product obtained in the step (2) to ion exchange chromatography to obtain a detection signal;
(4) determining whether the peak of the detection signal obtained in the step (3) is a peak indicating low methylated DNA or a peak indicating highly methylated DNA; and
(5) (i) determining the tissue or the cell as a tissue or a cell obtained from a patient free from a Lynch syndrome-associated tumor or unlikely to develop the Lynch syndrome-associated tumor when the peak is determined as a peak indicating highly methylated DNA in the step (4), or
(ii) determining the tissue or the cell as a tissue or a cell obtained from a patient suffering from a Lynch syndrome-associated tumor or likely to develop the Lynch syndrome-associated tumor when the peak is determined as a peak indicating low methylated DNA in the step (4).

In an additional embodiment, the present invention provides a method for determining a risk for the onset of a Lynch syndrome-associated tumor, comprising:
(1) treating genomic DNA prepared from a subject-derived tissue or cell with bisulfite;
(2) amplifying, by PCR, DNA comprising a portion or the whole of MLH1 promoter region from the bisulfite-treated DNA obtained in the step (1);
(3) subjecting the PCR amplification product obtained in the step (2) to ion exchange chromatography to obtain a detection signal;
(4) determining whether the peak of the detection signal obtained in the step (3) is a peak indicating low methylated DNA or a peak indicating highly methylated DNA; and
(5) (i) determining the subject as an individual free from a Lynch syndrome-associated tumor or unlikely to develop the Lynch syndrome-associated tumor when the peak is determined as a peak indicating highly methylated DNA in the step (4), or
(ii) determining the subject as an individual suffering from a Lynch syndrome-associated tumor or likely to develop the Lynch syndrome-associated tumor when the peak is determined as a peak indicating low methylated DNA in the step (4).

In an additional embodiment, the present invention provides a method for measuring methylated DNA for determining a risk for the onset of a Lynch syndrome-associated tumor, comprising:
(1) treating genomic DNA prepared from a subject-derived tissue or cell with bisulfite;
(2) amplifying, by PCR, DNA comprising a portion or the whole of MLH1 promoter region from the bisulfite-treated DNA obtained in the step (1);
(3) subjecting the PCR amplification product obtained in the step (2) to, ion exchange chromatography to obtain a detection signal; and
(4) determining whether the peak of the detection signal obtained in the step (3) is a peak indicating low methylated DNA or a peak indicating highly methylated DNA, wherein
the subject is determined as an individual free from a Lynch syndrome-associated tumor or unlikely to develop the Lynch syndrome-associated tumor when the peak is determined as a peak indicating highly methylated DNA in the step (4), or
the subject is determined as an individual suffering from a Lynch syndrome-associated tumor or likely to develop the Lynch syndrome-associated tumor when the peak is determined as a peak indicating low methylated DNA in the step (4).

In an additional embodiment, the present invention provides a method for obtaining data for determining a risk for the onset of a Lynch syndrome-associated tumor, comprising:
(1) treating genomic DNA prepared from a subject-derived tissue or cell with bisulfite;
(2) amplifying, by PCR, DNA comprising a portion or the whole of MLH1 promoter region from the bisulfite-treated DNA obtained in the step (1);
(3) subjecting the PCR amplification product obtained in the step (2) to ion exchange chromatography to obtain a detection signal; and
(4) obtaining whether the peak of the detection signal obtained in the step (3) is a peak indicating low methylated DNA or a peak indicating highly methylated DNA as data for determining whether or not the subject is suffering from a Lynch syndrome-associated tumor or whether the subject is likely or unlikely to develop the Lynch syndrome-associated tumor.

In an additional embodiment, the present invention provides a method for differentially diagnosing a tumor, comprising:
(1) treating genomic DNA prepared from a tumor-containing subject tissue or cell with bisulfite;
(2) amplifying, by PCR, DNA comprising a portion or the whole of MLH1 promoter region from the bisulfite-treated DNA obtained in the step (1);
(3) subjecting the PCR amplification product obtained in the step (2) to ion exchange chromatography to obtain a detection signal;
(4) determining whether the peak of the detection signal obtained in the step (3) is a peak indicating low methylated DNA or a peak indicating highly methylated DNA; and
(5) (i) determining the tumor as a tumor obtained from a patient without Lynch syndrome when the peak is determined as a peak indicating highly methylated DNA in the step (4), or
(ii) determining the tumor as a tumor obtained from a patient suspected of having Lynch syndrome when the peak is determined as a peak indicating low methylated DNA in the step (4).

In an additional embodiment, the present invention provides a method for differentially diagnosing a tumor patient, comprising:
(1) treating genomic DNA prepared from a subject-derived tumor-containing tissue or cell with bisulfite;
(2) amplifying, by PCR, DNA comprising a portion or the whole of MLH1 promoter region from the bisulfite-treated DNA obtained in the step (1);

(3) subjecting the PCR amplification product obtained in the step (2) to ion exchange chromatography to obtain a detection signal;
(4) determining whether the peak of the detection signal obtained in the step (3) is a peak indicating low methylated DNA or a peak indicating highly methylated DNA; and
(5) (i) determining the subject as having no Lynch syndrome when the peak is determined as a peak indicating highly methylated DNA in the step (4), or
(ii) determining the subject as suspected of having Lynch syndrome when the peak is determined as a peak indicating low methylated DNA in the step (4).

In an additional embodiment, the present invention provides a method for measuring methylated DNA for determining a tumor patient, comprising:
(1) treating genomic DNA prepared from a subject-derived tumor-containing tissue or cell with bisulfite;
(2) amplifying, by PCR, DNA comprising a portion or the whole of MLH1 promoter region from the bisulfite-treated DNA obtained in the step (1);
(3) subjecting the PCR amplification product obtained in the step (2) to ion exchange chromatography to obtain a detection signal; and
(4) determining whether the peak of the detection signal obtained in the step (3) is a peak indicating low methylated DNA or a peak indicating highly methylated DNA, wherein
the subject is determined as having no Lynch syndrome when the peak is determined as a peak indicating highly methylated DNA in the step (4), or
the subject is determined as suspected of having Lynch syndrome when the peak is determined as a peak indicating low methylated DNA in the step (4).

In an additional embodiment, the present invention provides a method for obtaining data for differentially diagnosing a tumor, comprising:
(1) treating genomic DNA prepared from a tumor-containing subject tissue or cell with bisulfite;
(2) amplifying, by PCR, DNA comprising a portion or the whole of MLH1 promoter region from the bisulfite-treated DNA obtained in the step (1);
(3) subjecting the PCR amplification product obtained in the step (2) to ion exchange chromatography to obtain a detection signal; and
(4) obtaining whether the peak of the detection signal obtained in the step (3) is a peak indicating low methylated DNA or a peak indicating highly methylated DNA as data for determining whether or not the tumor is a tumor obtained from a patient suspected of having Lynch syndrome.

Examples of the subject to which the additional embodiments of the present invention described above are applied include patients suspected of having a Lynch syndrome-associated tumor. Examples of the subject include patients found to have a tumor in the large intestine, the endometrium, the stomach, the ovarium, the small intestine, the bile duct, the pancreas, the renal pelvis, the urinary duct, the brain, or the sebaceous gland, and patients with the tumor treated, the patients being in need of determining whether or not the tumor is a Lynch syndrome-associated tumor. Alternative examples of the subject include individuals who are not affected by Lynch syndrome-associated tumor at the moment, but are in need of determining the risk for the onset (risk of developing) the Lynch syndrome-associated tumor in the future. In a preferred embodiment, examples of the subject include patients who have a tumor of the large intestine and are in need of determining the presence or absence of Lynch syndrome.

The subject tissue or cell used in the present embodiment can be any tissue or cell derived from the subject and is preferably a tissue or a cell of the large intestine, the endometrium, the stomach, the ovarium, the small intestine, the bile duct, the pancreas, the renal pelvis, the urinary duct, the brain, or the sebaceous gland. These tumors may be tumor-containing tissues or cells or may be non-tumor tissues or cells. A tumor-containing tissue or cell is used for determining whether or not the tumor found in the subject is a Lynch syndrome-associated tumor. In the case of determining the risk of developing a Lynch syndrome-associated tumor, any of a tumor-containing tissue or cell and a non-tumor tissue or cell may be used.

In any of the embodiments mentioned above, the subject tissue or cell can be, for example, a tissue or a cell collected by biopsy, surgical operation, or the like, a frozen product or a fixed preparation (formalin-fixed preparation, paraffin-embedded preparation, paraffin block, etc.) thereof, or a cultured cell. Blood can be used for the non-tumor tissue or cell. The method of the present invention is performed in vitro or ex vivo.

The method for preparing genomic DNA from the tissue or the cell is not particularly limited, and an approach known in the art can be appropriately selected for use. Examples of the method known in the art for preparing DNA include phenol-chloroform method, and DNA extraction method using a commercially available DNA extraction kit, for example, QIAamp(R) DNA Mini kit (manufactured by Qiagen N.V.), QIAamp(R) DNA FFPE Tissue Kit (manufactured by Qiagen N.V.), QIAamp(R) DNA Blood Maxi Kit (manufactured by Qiagen N.V.), Clean Columns (manufactured by Hermes-NexTec GmbH), AquaPure (manufactured by Bio-Rad Laboratories, Inc.), ZR Plant/Seed DNA Kit (manufactured by Zymo Research Corp.), prepGEM (manufactured by ZyGEM NZ, Ltd.), or BuccalQuick (manufactured by TrimGen Corp.).

Subsequently, the extracted genomic DNA is treated with bisulfite. The method for treating the DNA with bisulfite is not particularly limited, and an approach known in the art can be appropriately selected for use. Examples of the method known in the art for bisulfite treatment include methods using a commercially available kit, for example, EpiTect (R) Bisulfite Kit (48) (manufactured by Qiagen N.V.), MethylEasy (manufactured by Human Genetic Signatures Pty), Cells-to-CpG Bisulfite Conversion Kit (manufactured by Applied Biosystems, Inc.), or CpGenome Turbo Bisulfite Modification Kit (manufactured by Merck Millipore).

Subsequently, the bisulfite-treated genomic DNA is subjected to PCR to amplify the target DNA. The PCR amplification method is not particularly limited, and an approach known in the art can be appropriately selected for use according to the sequence, length, amount, etc. of the target DNA to be amplified.

DNA methylation reportedly occurs rarely in MLH1 promoter region in Lynch syndrome. Thus, in the method of the present invention, the target DNA to be amplified by PCR is preferably selected such that the DNA methylation in the MLH1 promoter region can be detected, and more preferably selected such that the methylation of the CpG island or CpG site of the MLH1 promoter region can be detected. For example, the target DNA is DNA comprising a portion or the whole of the MLH1 promoter region. The target DNA is more preferably DNA comprising a portion or the whole of the CpG island of the MLH1 promoter region.

MLH1 is a gene specified by RefSeq ID: NG_007109.2. The MLH1 promoter region is DNA consisting of the nucleotide sequence represented by SEQ ID NO: 1 shown in Table 1. Thus, in the method of the present invention, the target DNA to be amplified by PCR is preferably DNA consisting of the full-length nucleotide sequence represented by SEQ ID NO: 1 or a partial sequence thereof. More preferred examples of the target DNA include DNA comprising a region from bases 470 to 568, a region from bases 1 to 182, a region from bases 159 to 363, a region from bases 336 to 568, a region from bases 470 to 704, or a region from bases 684 to 841 in the nucleotide sequence represented by SEQ ID NO: 1. Further preferred examples thereof include DNA consisting of a region from bases 470 to 568, a region from bases 1 to 182, a region from bases 159 to 363, a region from bases 336 to 568, a region from bases 470 to 704, or a region from bases 684 to 841 in the nucleotide sequence represented by SEQ ID NO: 1. In the present invention, the target DNA encompasses 0 to 100% methylated DNA thereof.

TABLE 1

| Target gene name | Sequence |
| --- | --- |
| MLH1 promoter region | CTCTTCAGGA GTGAAGGAGG CCACGGGCAA GTCGCCCTGA CGCAGACGCT CCACCAGGGC CGCGCGCTCG CCGTCCGCCA CATACCGCTC GTAGTATTCG TGCTCAGCCT CGTAGTGGCG CCTGACGTCG CGTTCGCGGG TAGCTACGAT GAGGCGGCGA CAGACCAGGC ACAGGGCCCC ATCGCCCTCC GGAGGCTCCA CCACCAAATA ACGCTGGGTC CACTCGGGCC GGAAAACTAG AGCCTCGTCG ACTTCCATCT TGCTTCTTTT GGGCGTCATC CACATTCTGC GGGAGGCCAC AAGAGCAGGG CCAACGTTAG AAAGGCCGCA AGGGGAGAGG AGGAGCCTGA GAAGCGCCAA GCACCTCCTC CGCTCTGCGC CAGATCACCT CAGCAGAGGC ACACAAGCCC GGTTCCGGCA TCTCTGCTCC TATTGGCTGG ATATTTCGTA TTCCCCGAGC TCCTAAAAAC GAACCAATAG GAAGAGCGGA CAGCGATCTC TAACGCGCAA GCGCATATCC TTCTAGGTAG CGGGCAGTAG CCGCTTCAGG GAGGGACGAA GAGACCCAGC AACCCACAGA GTTGAGAAAT TTGACTGGCA TTCAAGCTGT CCAATCAATA GCTGCCGCTG AAGGGTGGGG CTGGATGGCG TAAGCTACAG CTGAAGGAAG AACGTGAGCA CGAGGCACTG AGGTGATTGG CTGAAGGCAC TTCCGTTGAG CATCTAGACG TTTCCTTGGC TCTTCTGGCG CCAAAATGTC GTTCGTGGCA GGGGTTATTC GGCGGCTGGA CGAGACAGTG GTGAACCGCA TCGCGGCGGG GGAAGTTATC CAGCGGCCAG CTAATGCTAT CAAAG (SEQ ID NO: 1) |

CpG sites are underlined.

The chain length of the target DNA to be amplified by PCR can be appropriately selected in consideration of factors such as reduction in PCR amplification time and reduction in analysis time in ion exchange chromatography, and maintenance of separation performance. In the method of the present invention, the chain length of the target DNA to be amplified by PCR is preferably 1,000 bp or shorter, more preferably 700 bp or shorter, further preferably 500 bp or shorter, still further preferably 300 bp or shorter. On the other hand, the chain length of the target DNA is preferably 30 to 40 bp or longer in order to avoid nonspecific hybridization in PCR. In a more preferred embodiment, the chain length of the target DNA is 50 to 500 bp, further preferably 70 to 300 bp.

Thus, in a preferred embodiment, the target DNA to be amplified by PCR in the method of the present invention is DNA consisting of the nucleotide sequence represented by SEQ ID NO: 1. In another preferred embodiment, the target DNA to be amplified by PCR in the method of the present invention is DNA consisting of a partial sequence of the nucleotide sequence represented by SEQ ID NO: 1 and having a base length of 50 to 500 bp, preferably 70 to 300 bp. In an alternative preferred embodiment, the target DNA to be amplified by PCR in the method of the present invention is a region which is amplified by a set of primers consisting of the nucleotide sequences represented by SEQ ID NOs: 6 and 7, SEQ ID NOs: 18 and 19, SEQ ID NOs: 20 and 22, SEQ ID NOs: 25 and 26, SEQ ID NOs: 29 and 28, or SEQ ID NOs: 30 and 32, in the DNA consisting of the nucleotide sequence represented by SEQ ID NO: 1.

Alternatively, when the deletion of the MLH1 protein caused by an acquired factor is suspected, the target DNA is selected such that the DNA methylation of the CpG island or CpG site of MLH1 promoter region and/or intron 1 region (SEQ ID NO: 33) (Cell Oncol., 36, 411-419, 2013) can be detected. For example, the target DNA is DNA comprising a portion or the whole of the MLH1 promoter region and/or the intron 1 region, more preferably DNA comprising a portion or the whole of the CpG island of the MLH1 promoter region and/or the intron 1 region.

In a preferred embodiment, the region and chain length of the target DNA are desirably determined such that the number of cytosine in the CpG site with respect to the total number of bases thereof is 2% or more, more preferably 5% or more.

Subsequently, the obtained PCR amplification product is subjected as sample DNA to ion exchange chromatography. The ion exchange chromatography according to the present invention is preferably anion exchange chromatography. The column packing material for use in the ion exchange chromatography according to the present invention is not particularly limited as long as the packing material is substrate particles having a strong cationic group on the surface. Substrate particles having both a strong cationic group and a weak cationic group on the surface of the packing material as shown in WO 2012/108516 are preferred.

In the present specification, the strong cationic group means a cationic group which is dissociated in a wide pH range of from 1 to 14. Specifically, the strong cationic group can maintain its dissociated (cationized) state without being influenced by the pH of an aqueous solution.

Examples of the strong cationic group include quaternary ammonium groups. Specific examples thereof include trialkylammonium groups such as a trimethylammonium group, a triethylammonium group, and a dimethylethylammonium group. Examples of the counter ion for the strong cationic group include halide ions such as a chloride ion, a bromide ion, and an iodide ion.

The amount of the strong cationic group introduced to the surface of the substrate particles is not particularly limited and is preferably 1 µeq/g as the lower limit and 500 µeq/g as the upper limit with respect to the dry weight of the packing material. If the amount of the strong cationic group is less than 1 µeq/g, separation performance may be deteriorated due to weak retention strength. If the amount of the strong cationic group exceeds 500 µeq/g, retention strength may be too strong to easily elute the sample DNA, resulting in problems such as too long an analysis time.

In the present specification, the weak cationic group means a cationic group having pka of 8 or higher. Specifically, the weak cationic group changes its dissociated state by the influence of the pH of an aqueous solution. Specifically, at pH higher than 8, the proton of the weak cationic group is dissociated so that the ratio of a group having no positive charge is increased. On the other hand, at pH lower than 8, the weak cationic group is protonated so that the ratio of a group having positive charge is increased.

Examples of the weak cationic group include tertiary amino groups, secondary amino groups, and primary amino groups. Among them, a tertiary amino group is desirable.

The amount of the weak cationic group introduced to the surface of the substrate particles is not particularly limited and is preferably 0.5 µeq/g as the lower limit and 500 µeq/g as the upper limit with respect to the dry weight of the packing material. If the amount of the weak cationic group is less than 0.5 µeq/g, separation performance may not be improved due to too small an amount. If the amount of the weak cationic group exceeds 500 µeq/g, retention strength may be too strong to easily elute the sample DNA, resulting in problems such as too long an analysis time, as with the strong cationic group.

The amount of the strong cationic group or the weak cationic group on the surface of the substrate particles can be measured by quantifying a nitrogen atom contained in an amino group. Examples of the method for quantifying nitrogen include Kjeldahl method. In the case of the packing material described in the present invention (Examples), first, nitrogen contained in the strong cationic group after polymerization is quantified. Subsequently, nitrogen contained in the strong cationic group and the weak cationic group after introduction of the weak cationic group is quantified. As a result, the amount of the weak cationic group introduced later can be calculated. Such quantification allows the amount of the strong cationic group and the amount of the weak cationic group to be adjusted within the ranges described above for preparing the packing material.

For example, synthetic polymer fine particles obtained using polymerizable monomers or the like, or inorganic fine particles such as fine silica particles can be used as the substrate particles. Hydrophobic cross-linked polymer particles consisting of a synthetic organic polymer are desirable.

The hydrophobic cross-linked polymer may be any of a hydrophobic cross-linked polymer obtained by copolymerizing at least one hydrophobic cross-linkable monomer and at least one monomer having a reactive functional group, and a hydrophobic cross-linked polymer obtained by copolymerizing at least one hydrophobic cross-linkable monomer, at least one monomer having a reactive functional group, and at least one hydrophobic non-cross-linkable monomer.

The hydrophobic cross-linkable monomer is not particularly limited as long as the monomer has two or more vinyl groups in one molecule. Examples thereof include: di(meth)acrylic acid esters such as ethylene glycol di(meth)acrylate, polyethylene glycol di(meth)acrylate, propylene glycol di(meth)acrylate, and polypropylene glycol di(meth)acrylate; tri(meth)acrylic acid esters such as trimethylol methane tri(meth)acrylate and tetramethylol methane tri(meth)acrylate; tetra(meth)acrylic acid esters; and aromatic compounds such as divinylbenzene, divinyltoluene, divinylxylene, and divinylnaphthalene. In the present specification, the (meth)acrylate means acrylate or methacrylate, and (meth)acryl means acryl or methacryl.

Examples of the monomer having a reactive functional group include glycidyl (meth)acrylate and isocyanatoethyl (meth)acrylate.

The hydrophobic non-cross-linkable monomer is not particularly limited as long, as the monomer is a non-cross-linkable polymerizable organic monomer having hydrophobic properties. Examples thereof include: (meth)acrylic acid esters such as methyl (meth)acrylate, ethyl (meth)acrylate, butyl (meth)acrylate, and t-butyl (meth)acrylate; and styrene monomers such as styrene and methylstyrene.

When the hydrophobic cross-linked polymer is obtained by copolymerizing the hydrophobic cross-linkable monomer and the monomer having a reactive functional group, the content ratio of a segment derived from the hydrophobic cross-linkable monomer in the hydrophobic cross-linked polymer is preferably 10 wt % as the lower limit, more preferably 20 wt % as the lower limit.

The packing material for the ion exchange chromatography used in the present invention preferably has a polymer layer having the strong cationic group and the weak cationic group on the surface of the substrate particles. For the polymer having the strong cationic group and the weak cationic group, it is preferred that the strong cationic group and the weak cationic group should be respectively derived from independent monomers. Specifically, the packing material for the ion exchange chromatography used in the present invention is preferably a packing material in which the weak cationic group is introduced in the surface of coated polymer particles consisting of the hydrophobic cross-linked polymer particles and a layer of a hydrophilic polymer having the strong cationic group copolymerized at the surface of the hydrophobic cross-linked polymer particles.

The hydrophilic polymer having the strong cationic group is formed from hydrophilic monomers having the strong cationic group and can contain a segment derived from one or more hydrophilic monomers having the strong cationic group. Specifically, examples of the method for producing the hydrophilic polymer having the strong cationic group include a method which involves homopolymerizing a hydrophilic monomer having the strong cationic group, a method which involves copolymerizing two or more hydrophilic monomers each having the strong cationic group, and a method which involves copolymerizing a hydrophilic monomer having the strong cationic group and a hydrophilic monomer having no strong cationic group.

The hydrophilic monomer having the strong cationic group preferably has a quaternary ammonium group. Specific examples thereof include ethyl methacrylate triethylammonium chloride, ethyl methacrylate dimethylethylammonium chloride, ethyl methacrylate dimethylbenzylammonium chloride, ethyl acrylate dimethylbenzylammonium chloride, ethyl acrylate triethylammonium chloride, ethyl acrylate dimethylethylammonium chloride, acrylamide ethyltrimethylammonium chloride, acrylamide ethyltriethylammonium chloride, and acrylamide ethyl dimethylethylammonium chloride.

A method known in the art can be used as a method for introducing the weak cationic group to the surface of the coated polymer particles. Specifically, examples of the method for introducing a tertiary amino group as the weak cationic group include: a method which involves copolymerizing the hydrophilic monomer having the strong cationic group at the surface of the hydrophobic cross-linked polymer particles consisting of a hydrophobic cross-linked polymer having a segment derived from a monomer having a glycidyl group, and subsequently reacting the glycidyl group with a reagent having a tertiary amino group; a method which involves copolymerizing the hydrophilic monomer having the strong cationic group at the surface of the hydrophobic cross-linked polymer particles consisting of a hydrophobic cross-linked polymer having a segment derived from a monomer having an isocyanate group, and subsequently reacting the isocyanate group with a reagent having a tertiary amino group; a method Which involves copolymerizing the hydrophilic monomer having the strong cationic group and a monomer having a tertiary amino group at the surface of the hydrophobic cross-linked polymer particles; a method which involves introducing a tertiary amino group to the surface of the coated polymer particles having a hydrophilic polymer layer having the strong cationic group using a silane coupling agent having the tertiary amino group; a method which involves copolymerizing the hydrophilic monomer having the strong cationic group at the surface of the hydrophobic dross-linked polymer particles consisting of a hydrophobic cross-linked polymer having a segment derived from a monomer having a carboxy group, and subsequently condensing the carboxy group with a reagent having a tertiary amino group using carbodiimide; and a method which involves copolymerizing the hydrophilic monomer having the strong cationic group at the surface of the hydrophobic cross-linked polymer particles consisting of a hydrophobic cross-linked polymer having a segment derived from a monomer having an ester bond, hydrolyzing the ester bond moiety, and then condensing a carboxy group formed by the hydrolysis with a reagent having a tertiary amino group using carbodiimide. Among them, the method which involves copolymerizing the hydrophilic monomer having the strong cationic group at the surface of the hydrophobic cross-linked polymer particles consisting of a hydrophobic cross-linked polymer having a segment derived from a monomer having a glycidyl group, and subsequently reacting the glycidyl group with a reagent having a tertiary amino group, or the method which involves copolymerizing the hydrophilic monomer having the strong cationic group at the surface of the hydrophobic cross-linked polymer particles consisting of a hydrophobic cross-linked polymer having a segment derived from a monomer having an isocyanate group, and subsequently reacting the isocyanate group with a reagent having a tertiary amino group, is preferred.

The reagent having a tertiary amino group which is reacted with the reactive functional group such as a glycidyl group or an isocyanate group is not particularly limited as long as the reagent has a functional group reactable with the tertiary amino group and the reactive functional group. Examples of the functional group reactable with the reactive functional group include primary amino groups and a hydroxy group. Among others, a group having a terminal primary amino group is preferred. Specific examples of the reagent having the functional group include N,N-dimethylaminomethylamine, N,N-dimethylaminoethylamine, N,N-dimethylaminopropylamine, N,N-dimethylaminobutylamine, N,N-diethylaminoethylamine, N,N-diethylaminopropylethylamine, N,N-diethylaminobutylamine, N,N-diethylaminopentylamine, N,N-diethylaminohexylamine, N,N-dipropylaminobutylamine, and N,N-dibutylaminopropylamine.

For the relative positional relationship between the strong cationic group (preferably, a quaternary ammonium salt) and the weak cationic group (preferably, a tertiary amino group), it is preferred that the strong cationic group should be positioned more distant than the weak cationic group from the surface of the substrate particles, i.e., positioned on the outer side of the weak cationic group. Preferably, for example, the weak cationic group is located within 30 angstroms from the surface of the substrate particles, and the strong cationic group is located within 300 angstroms from the surface of the substrate particles and on the outer side of the weak cationic group.

The average particle size of the substrate particles which are used as the packing material for the ion exchange chromatography used in the present invention is not particularly limited and is preferably 0.1 μm as the lower limit and 20 μm as the upper limit. If the average particle size is less than 0.1 μm, poor separation may occur due to too high an intra-column pressure. If the average particle size exceeds 20 μm, poor separation may occur due to too large an intra-column dead volume. In the present specification, the average particle size refers to a volume-average particle size and can be measured using a particle size distribution measurement apparatus (e.g., AccuSizer 780, manufactured by Particle Sizing Systems).

Conditions known in the art can be used for the composition of an eluent for use in the ion exchange chromatography according to the present invention.

The buffer solution for use in the eluent is preferably a buffer solution containing a salt compound known in the art, or an organic solvent. Specific examples thereof include a tris-HCl buffer solution, a TE buffer solution consisting of tris and EDTA, and a TBA buffer solution consisting of tris, boric acid, and EDTA.

The pH of the eluent is not particularly limited and is preferably 5 as the lower limit and 10 as the upper limit. At the pH set to within this range, the weak cationic group is considered to also work effectively as an ion exchange group (anion exchange group). The pH of the eluent is more preferably 6 as the lower limit and 9 as the upper limit.

Examples of the salt contained in the eluent include: salts consisting of a halide and an alkali metal, such as sodium chloride, potassium chloride, sodium bromide, and potassium bromide; and salts consisting of a halide and an alkaline earth metal, such as calcium chloride, calcium bromide, magnesium chloride, and magnesium bromide; and inorganic acid salts such as sodium perchlorate, potassium perchlorate, sodium sulfate, potassium sulfate, ammonium sulfate, sodium nitrate, and potassium nitrate. Alternatively, an organic acid salt such as sodium acetate, potassium acetate, sodium succinate, or potassium succinate may be used. Any one of these salts may be used alone or, two or more thereof may be used in combination.

The salt concentration of the eluent can be appropriately adjusted according to analysis conditions and is preferably 10 mmol/L as the lower limit and 2,000 mmol/L as the upper limit, more preferably 100 mmol/L as the lower limit and 1,500 mmol/L as the upper limit.

The eluent for use in the ion exchange chromatography used in the present invention further contains an anti-chaotropic ion for further enhancing separation performance. The anti-chaotropic ion has properties opposite to those of a chaotropic ion and works to stabilize a hydrated structure. Therefore, the anti-chaotropic ion is effective for strengthening the hydrophobic interaction between the packing material and a nucleic acid molecule. The main interaction of the ion exchange chromatography used in the present invention is electrostatic interaction. Separation performance is enhanced through the use of the work of the hydrophobic interaction in addition thereto.

Examples of the anti-chaotropic ion contained in the eluent include a phosphate ion ($PO_4^{3-}$), a sulfate ion ($SO_4^{2-}$), an ammonium ion ($NH_4^+$), a potassium ion ($K^+$), and a sodium ion ($Na^+$). Among combinations of these ions, a sulfate ion and an ammonium ion are preferably used. Any one of these anti-chaotropic ions may be used alone, or two or more thereof may be used in combination. Some of the anti-chaotropic ions mentioned above comprise a salt contained in the eluent or a component of the buffer solution. Use of such a component is suitable for the present invention, because the component possesses both of properties or buffering ability as the salt contained in the eluent and properties as the anti-chaotropic ion.

The concentration at the time of analysis of the anti-chaotropic ion in the eluent for the ion exchange chromatography used in the present invention can be appropriately adjusted according to an analyte and is desirably 2,000 mmol/L or lower in terms of anti chaotropic salt. Specific examples of such a method can include a method which involves performing gradient elution at anti-chaotropic salt concentrations ranging from 0 to 2,000 mmol/L. Thus, the concentration of the anti-chaotropic salt at the start of analysis does not have to be 0 mmol/L, and the concentration of the anti-chaotropic salt at the completion of analysis does not have to be 2,000 mmol/L. The gradient elution method may be a low-pressure gradient method or may be a high-pressure gradient method. The method preferably involves performing elution while the concentration is precisely adjusted by the high-pressure gradient method.

The anti-chaotropic ion may be added to only one eluent for use in elution or may be added to a plurality of eluents. Also, the anti-chaotropic ion may playa role both in the effect of enhancing the hydrophobic interaction between the packing material and the sample DNA or the buffering ability and in the effect of eluting the sample DNA from the column.

The column temperature for analyzing the sample DNA by the ion exchange chromatography according to the present invention is preferably 30° C. or higher, more preferably 40° C. or higher, further preferably 45° C. or higher. If the column temperature in the ion exchange chromatography is lower than 30° C., the hydrophobic interaction between the packing material and the sample DNA is weakened, and the desired separating effect is difficult to obtain. If the column temperature in the ion exchange chromatography is lower than 45° C., the PCR amplification product of bisulfite-treated methylated DNA (methylated DNA sample) and the PCR amplification product of bisulfite-treated unmethylated DNA (unmethylated DNA sample) do not much differ in retention time. When the column temperature is 60° C. or higher, the methylated DNA sample and the unmethylated DNA sample differ more largely in retention time and respectively exhibit more clear peaks. Therefore, DNA methylation can be detected more accurately.

As the column temperature in the ion exchange chromatography is higher, the methylated DNA sample and the unmethylated DNA sample are more clearly separable. Therefore, the methylated DNA and the unmethylated DNA tend to differ in their peak areas or peak heights at retention times according to their abundance ratios in the target DNA. Thus, at a higher column temperature, the respective abundances or abundance ratios of the methylated DNA and the unmethylated DNA in the target DNA can be measured more easily on the basis of the difference between the peak areas or heights at retention times of the methylated DNA sample and the unmethylated DNA sample.

On the other hand, a column temperature of 90° C. or higher in the ion exchange chromatography is not preferred for the analysis because two strands' of the nucleic acid molecule in the sample DNA are dissociated. A column temperature of 100° C. or higher is not preferred for the analysis because the eluent might be boiled. Thus, the column temperature for analyzing the sample DNA by the ion exchange chromatography according to the present invention can be 30° C. or higher and lower than 90° C. and is preferably 40° C. or higher and lower than 90° C., more preferably 45° C. or higher and lower than 90° C., further preferably 55° C. or higher and lower than 90° C., still further preferably 55° C. or higher and 85° C. or lower, particularly preferably 60° C. or higher and 85° C. or lower.

The sample injection volume to the ion exchange chromatography column is not particularly limited and can be appropriately adjusted according to the ion exchange capacity of the column and the sample concentration. The flow rate is preferably from 0.1 mL/min to 3.0 mL/min, more preferably from 0.5 mL/min to 1.5 mL/min. At a slower flow rate, improved separation can be expected. Too slow a flow rate might require a long time for analysis or incur reduction in separation performance due to broader peaks. On the other hand, a faster flow rate is advantageous in terms of reduction in analysis time, but incurs reduction in separation performance due to peak compression. Accordingly, it is desirable to set the flow rate to within the range described above, though this parameter is appropriately adjusted according to the performance of the column. The retention time of each sample can be predetermined by a preliminary experiment on each sample. A flowing method known in the art, such as linear gradient elution method or stepwise elution method can be used. The flowing method according to the present invention is preferably linear gradient elution method. The amplitude of the gradient can be appropriately adjusted within a range of the eluent for use in elution from 0% to 100% according to the separation performance of the column and the characteristics of the analyte (here, the sample DNA).

In the present invention, the PCR amplification product of the bisulfite-treated target DNA (i.e., sample DNA) is subjected to ion exchange chromatography by the procedures described above.

The treatment of DNA with bisulfite converts unmethylated cytosine in the DNA to uracil, while leaving methylated cytosine unaltered. The PCR amplification of the bisulfite-treated DNA further replaces uracil derived from the unmethylated cytosine with thymine and therefore results in the difference in the abundance ratios of cytosine and thymine between methylated DNA and unmethylated DNA. Thus, the sample DNA has a distinctive sequence according to the methylation rate of the original target DNA. The sample DNA is subjected to ion exchange chromatography to obtain a chromatogram showing a distinctive signal according to its nucleotide sequence. Thus, the methylation of the target DNA can be detected on the basis of a detection signal obtained by the ion exchange chromatography of the sample DNA.

The presence or absence of methylated DNA in sample DNA can be measured, for example, by comparing a detection signal from the PCR amplification product of the bisulfite-treated target DNA (i.e., sample DNA) with a detection signal from the PCR amplification product of bisulfite-treated DNA having the same nucleotide sequence, albeit not methylated, as that of the target DNA (hereinafter, this PCR amplification product is referred to as a negative control), or a detection signal from the PCR amplification product of bisulfite-treated DNA having the same nucleotide sequence as that of the target DNA and having a known methylation rate (e.g., 100%) (hereinafter, this PCR amplification product is referred to as a positive control).

Alternatively, the ratio between the abundance of methylated DNA and the abundance of unmethylated DNA in target DNA can be measured by comparing a detection signal from the sample DNA with detection signals from the negative and positive controls. Alternatively, the methylation rate of methylated DNA, its abundance, and the ratio between the abundance of methylated DNA and the abundance of unmethylated DNA in target DNA can be measured by comparing detection signals from a plurality of PCR amplification products derived from a plurality of bisulfite-treated DNAs each having the same nucleotide sequence as that of the target DNA and having a known methylation rate (hereinafter, these PCR amplification products are referred to as standards) with a detection signal from the sample DNA.

Thus, the methylation of the target DNA can be detected by comparing a detection signal from the sample DNA obtained in the chromatography with a detection signal from the negative or positive control, or the standards, on the basis of difference between their detection signals.

DNA synthesized chemically or in a genetic engineering manner may be used as the DNA of the negative control, the positive control, or the standards. A commercially available product can also be used in the preparation of the negative control, the positive control, and the standards, and, for example, EpiTect (R) Control DNA and Control DNA Set (manufactured by Qiagen N.V.) can be used.

For example, in the ion exchange chromatography, the sample DNA and the negative control, the positive control, or the standards can be individually subjected to ion exchange chromatography analysis. The samples adsorbed on the column can be applied to gradient elution using a plurality of eluents to elute the sample DNA and the negative control, the positive control, or the standards at different retention times according to their DNA methylation rates.

The detection signal from the negative control can be acquired by performing bisulfite treatment and PCR according to the procedures mentioned above using DNA having the same nucleotide sequence, albeit not methylated, as that of the target DNA instead of the sample DNA and subjecting the obtained PCR amplification product to ion exchange chromatography. The detection signal from the positive control can be acquired by performing bisulfite treatment and PCR according to the procedures mentioned above using DNA having the same nucleotide sequence as that of the target DNA and having a known methylation rate (e.g., 100%) instead of the sample DNA and subjecting the obtained PCR amplification product to ion exchange chromatography. Alternatively, the detection signal from the negative or positive control may be obtained by subjecting the synthesized DNA or the commercially available DNA mentioned above as the negative or positive control to ion exchange chromatography.

For example, the target DNA can be determined as methylated when the peak retention time of the detection signal obtained from the sample DNA deviates from the peak retention time of the negative control. In this respect, as the deviation of the retention time is larger, the methylation rate can be presumed to be larger. On the other hand, as the peak retention time of the detection signal obtained from the sample DNA deviates more largely from the peak retention time of the 100% methylated positive control, the methylation rate of the target DNA can be presumed to be smaller.

The detection signals from the standards can be acquired by performing bisulfite treatment and PCR according to the procedures mentioned above using a plurality of DNAs each having the same nucleotide sequence as that of the target DNA and having a known methylation rate instead of the sample DNA and subjecting each of a plurality of the obtained PCR amplification products to ion exchange chromatography. Furthermore, a calibration curve may be prepared from the respective detection signals thus obtained. Alternatively, the detection signals from the standards may be obtained by subjecting the synthesized DNA or the commercially available DNA mentioned above as the standards to ion exchange chromatography. The calibration curve can establish an association between DNA methylation rates and retention times. Thus, a DNA methylation rate can be determined on the basis of the calibration curve.

Also, the abundance ratio of methylated DNA (e.g., the abundance ratio of unmethylated DNA or the abundance ratio of DNA methylated at a particular rate) in target DNA can be determined, for example, by comparing the peak height or the peak area of the detection signal obtained from the sample DNA with the peak height or the peak area of a detection signal obtained from the PCR amplification product of bisulfite-treated DNA having a known methylation rate and mixing ratio of methylated DNA.

In one embodiment, the DNA methylation rate in the method of the present invention can be determined with reference to a two-point calibration curve prepared by an association between the peak retention times of a positive control (100% methylated DNA) and a negative control (0% methylated DNA) and DNA methylation rates. In this case, an average retention time of the positive control and the negative control is defined as the retention time (reference value) of DNA having a methylation rate of 50%. Sample DNA can be determined as highly methylated DNA when the peak retention time of a detection signal obtained from the sample DNA is equal to or shorter than the reference value, and can be determined as low methylated DNA when the peak retention time of a detection signal obtained from the sample DNA is longer than the reference value.

In the case of determining a peak, the lower limit of quantification, preferably the lower limit of detection, is determined from a chromatography detection signal according to the general rules for ion chromatography under JIS K 0127:2013. The shape of the peak is determined from the degree of separation of the peak and the slope of a chromatogram. Examples of the method for determining the presence or absence of the peak of the detection signal obtained by the chromatography include peak detection using existing data processing software, for example, LCsolution (Shimadzu Corp.), GRAMS/AI (Thermo Fisher Scientific, Inc.), or Igor Pro (WaveMetrics). The method for determining the presence or absence of the peak using LCsolution will be described as an example. Specifically, a retention time zone in which a peak is to be detected is first designated. Next, various parameters are set in order to remove unnecessary peaks such as noise. Examples of such settings include setting of the parameter "WIDTH" to larger than the half widths of unnecessary peaks, setting of the parameter "SLOPE" to larger than the leading slopes of unnecessary peaks, and changing of the parameter "DRIFT" setting to select either vertical partitioning or baseline partitioning of peaks with a low degree of separation. The values of these parameters can be set to appropriate values according to a chromatogram because the obtained chromatogram differs depending on analysis conditions, the type of a selected gene marker, the amount of a specimen, etc. The peak is preferably determined within a retention time range including the respective rises and falls of the peak of DNA having a methylation rate of 0% and the peak of DNA having a methylation rate of 100%. When a plurality of peaks are detected from the sample DNA, the retention time of a peak most analogous to the peak of the positive control may be adopted as the retention time of the sample DNA. Alternatively, an average retention time of these peaks may be adopted as the retention time of the whole sample DNA.

The retention time, i.e., peak top time, can be automatically calculated using the data processing software. For example, first derivation of the chromatogram is carried out, and the time at which the derivative changes from positive to negative can be obtained as the peak top time.

The presence or absence of Lynch syndrome in the subject can be determined by screening on the basis of the retention time of the detection signal obtained by the chromatography. For example, the target DNA has a high methylation rate when the obtained detection signal has a peak at a short retention time as shown by a T specimen in FIG. 1 as a result of the chromatography of the sample DNA. This indicates that the target DNA is derived from a tissue or a cell containing a tumor silenced by methylation. On the other hand, the target DNA has a low methylation rate when the obtained detection signal has a peak at a long retention time as shown by a T specimen in FIG. 2 as a result of the chromatography of the sample DNA. This indicates that the target DNA is derived from a tissue or a cell containing a tumor unsilenced by methylation.

According to the present invention, whether or not a tumor contained in a subject tissue or cell is a Lynch syndrome-associated tumor can be determined on the basis of the peak of a chromatography detection signal froth sample DNA derived from the tumor-containing subject tissue or cell as obtained by the procedures described above. For example, the tumor is determined as nota Lynch syndrome-associated tumor when the peak of the detection signal is a peak indicating highly methylated DNA. On the other hand, the tumor is determined as a suspected Lynch syndrome-associated tumor when the peak of the detection signal is not a peak indicating highly methylated DNA (e.g., when the peak of the detection signal is a peak indicating low methylated DNA). Alternatively, the subject having the tumor is determined as having no Lynch syndrome when the peak of the detection signal is a peak indicating highly methylated DNA. On the other hand, the subject having the tumor is determined as suspected of having Lynch syndrome when the peak of the detection signal is not a peak indicating highly methylated DNA (e.g., when the peak of the detection signal is a peak indicating low methylated DNA).

Alternatively, the risk of developing a Lynch syndrome-associated tumor in a subject can be determined on the basis of the peak of a detection signal obtained by the chromatography of Sample DNA derived from a non-tumor tissue or cell of the subject as obtained by the procedures described above. For example, the subject is determined as having a low risk of developing a Lynch syndrome-associated tumor when the peak of the detection signal is a peak indicating highly methylated DNA. On the other hand, the subject is determined as having a high risk of developing a Lynch syndrome-associated tumor when the peak of the detection signal is not a peak indicating highly methylated DNA (e.g., when the peak of the detection signal is a peak indicating low methylated DNA).

Accordingly, in the present invention, the sample DNA whose peak of the chromatography detection signal is a peak indicating highly methylated DNA is selected as a candidate of DNA which is not derived from a subject suffering from a Lynch syndrome-associated tumor or having a high risk of developing the Lynch syndrome-associated tumor, or DNA which is not derived from a tissue or a cell derived from the subject. On the other hand, the sample DNA whose peak of the chromatography detection signal is not a peak indicating highly methylated DNA is selected as a candidate of DNA derived from a subject suffering from Lynch syndrome or having a high risk of developing Lynch syndrome, or DNA derived from a tissue or a cell of the subject.

The determination of the presence or absence of Lynch syndrome in the tumor or the subject, and the determination of the risk of developing a Lynch syndrome-associated tumor according to the present invention can be carried out by MSI examination on a tumor collected from the subject, in addition to the DNA methylation measurement. The subject is more likely to be a Lynch syndrome patient when the tumor is microsatellite instability-positive (MSI-H) as a result of the MSI examination. Thus, the combination of the DNA methylation measurement and the MSI examination enables more accurate determination of the presence or absence of Lynch syndrome in the subject or the risk of developing a Lynch syndrome-associated tumor in the subject.

In the MSI examination, genomic DNA collected from each of a tumor tissue or cell and a non-tumor tissue or cell of the subject is subjected to the MSI examination. In the MSI examination, the number of microsatellite repeats detected by microsatellite markers is compared between the tumor tissue or cell and the non-tumor tissue or cell. The tumor is determined as having MSI when the number of repeats different between the tumor tissue or cell and the non-tumor tissue or cell is detected by any of the markers, and determined as having MSI-H when MSI is detected by two or more types of markers. The subject is determined as a Lynch syndrome patient, or the tissue or the cell of the subject is determined as a tissue or a cell obtained from a Lynch syndrome patient, when the tumor has MSI-H as a result of the MSI examination and the peak of the detection signal obtained by the chromatography is a peak indicating low methylated DNA. Alternatively, the subject is determined as having a high risk of developing a Lynch syndrome-associated tumor. The microsatellite markers for use in the MSI examination are not particularly limited as long as the microsatellite markers are generally used in clinical MSI examination. BAT25, BAT26, D2S123, D5S346, and D17S250 are preferred.

The genomic DNA of the tumor tissue or cell to be subjected to the MSI examination may be the genomic DNA prepared for the bisulfite treatment or may be newly prepared from the same subject. The tissue or the cell of the subject for use in newly preparing the genomic DNA can be any tumor-containing tissue and may be a tissue or a cell of the same type with or a different type from that used in the preparation of the genomic DNA for the bisulfite treatment. The MSI examination may be carried out before or after the DNA methylation measurement.

Alternatively, the immunohistochemical examination of the tumor may be performed instead of the MSI examination or in addition to the MSI examination. The subject is determined as a Lynch syndrome patient, or the tissue or the cell of the subject is determined as a tissue or a cell obtained from a Lynch syndrome patient, when no or reduced expression of MLH1 is determined in the immunohistochemical examination of the tumor tissue or cell. Alternatively, the subject is determined as having a high risk of developing a Lynch syndrome-associated tumor. The tumor tissue or cell to be subjected to the immunohistochemical examination may be the same tissue or cell as that used in the preparation of the genomic DNA for the bisulfite treatment or may be newly prepared from the same subject.

Alternatively, screening for Lynch syndrome according to the Amsterdam Criteria II or the revised Bethesda Guidelines may be carried out instead of the MSI examination and/or the immunohistochemical examination. The subject is determined as a Lynch syndrome patient, or the tissue or the cell of the subject is determined as a tissue or a cell obtained from a Lynch syndrome patient, when results of the screening indicate suspected Lynch syndrome and the peak of the detection signal obtained by the chromatography is a peak indicating low methylated DNA. Alternatively, the subject is determined as having a high risk of developing a Lynch syndrome-associated tumor.

The subject determined as a Lynch syndrome patient by the combination of the chromatography and the MSI examination and/or the immunohistochemical examination may receive a definitive diagnosis by genetic examination. As shown in the JSCCR Guidelines for the Clinical Practice of Hereditary Colorectal Cancer, the definitive diagnosis of Lynch syndrome is made by identifying a deleterious mutation by the genetic examination (germline gene analysis) of a mismatch repair gene (Japanese Society for Cancer of the Colon and Rectum "the JSCCR Guidelines 2012 for the Clinical Practice of Hereditary Colorectal Cancer", Kanehara & Co., Ltd., 2012). The biological sample for use in the genetic examination of a mismatch repair gene is any tissue containing the gene without limitations. Lymphocytes obtained by blood collection are generally used because of low invasiveness. Direct sequencing is generally used as the method for analyzing the gene. If the mutation is not detected, a portion of the gene might be largely lost or duplicated, or might be reconstituted. Therefore, the gene is further analyzed by use of MLPA (multiplex ligation-dependent probe amplification), Southern blot, or the like.

The method of the present invention can be applied to confirmation that the subject has no Lynch syndrome, when the subject in the method of the present invention is a patient affected by a tumor and determined as (i) having MSI-H of the tumor in MSI examination and/or no or reduced expression of MLH1 in the tumor in immunohistochemical examination, and (ii) having no mutation in MLH1 in genetic examination. Specifically, the tumor is determined as not a Lynch syndrome-associated tumor, or the subject having the tumor is determined as having no Lynch syndrome, when the peak of the detection signal from the sample DNA obtained by the chromatography is a peak indicating highly methylated DNA. Alternatively, the sample DNA whose peak of the chromatography detection signal is a peak indicating highly methylated DNA is selected as DNA which is not derived from a Lynch syndrome patient. This method is useful in differential diagnosis for denying the possibility of Lynch syndrome in a patient manifesting no abnormality in MLH1 in conventional genetic examination.

EXAMPLES

Hereinafter, the present invention will be described in detail with reference to Examples. However, the present invention is not intended to be limited by Examples given below.

[Patient and Tissue Sample]

Surgical colorectal cancer preparations (tumor; hereinafter, referred to as a T specimen or T) and peripheral blood (normal; hereinafter, referred to as a N specimen or N) obtained from 4 patients, possessed by the Cancer Institute Hospital of JFCR (Koto, Tokyo, Japan) were each analyzed. The T specimen was a paraffin block. These patients were classified into groups 1 to 4 described below. Each group was subjected to DNA methylation analysis by pyrosequencing to reveal that the groups 1 and 4 were methylation-positive groups, and the groups 2 and 3 were methylation-negative groups.

Group 1: Patient ID: S-1

A colorectal cancer patient of a constitutional epimutation case.

This patient was confirmed to have highly methylated MLH1 of the germline. In the T specimen of the patient, it was confirmed that one allele was highly methylated and the other allele was highly methylated or lost due to LOH (loss of heterozygosity). In the N specimen of the patient, it was confirmed that only one allele was highly methylated.

Group 2: Patient ID: S-2

A Lynch syndrome patient.

This patient was confirmed to be positive (MSI-H) in microsatellite instability examination, have almost no methylation of MLH1, and have a mutation in MLH1.

Group 3: Patient ID: S-3

A colorectal cancer patient of an ordinary case.

This patient was confirmed to be negative (MSS) in microsatellite instability examination and have almost no MLH1 methylation.

Group 4: Patient ID: S-4

A colorectal cancer patient.

This patient was confirmed to be positive (MSI-H) in microsatellite instability examination, have the disappearance of MLH1 protein expression in immunohistochemical examination, and have highly methylated MLH1 promoter region in a pyrosequencer.

[Reference Example 1] Detection of Methylated DNA by Ion Exchange Chromatography (1) Preparation of Anion Exchange Column In a reactor equipped with: a stirrer, a mixture of 200 g of tetraethylene glycol dimethacrylate (manufactured by Shin-Nakamura Chemical Co., Ltd.), 100 g of triethylene glycol dimethacrylate (manufactured by Shin-Nakamura Chemical Co., Ltd.), 100 g of glycidyl methacrylate (manufactured by Wako Pure Chemical Industries, Ltd.), and 1.0 g of benzoyl peroxide (manufactured by Kishida Chemical Co., Ltd.) was added to 2,000 mL of an aqueous solution containing 3 wt % of polyvinyl alcohol (manufactured by The Nippon Synthetic Industry Co., Ltd.). The reaction mixture was heated with stirring and polymerized at 80° C. for 1 hour in the nitrogen atmosphere. Next, 100 g of ethyl methacrylate trimethylammonium chloride (manufactured by Wako Pure Chemical Industries, Ltd.) was dissolved as the hydrophilic monomer having the strong cationic group in ion exchange water. This solution was added to the reactor mentioned above. Similarly, the reaction mixture was polymerized with stirring at 80° C. for 2 hours in the nitrogen atmosphere. The obtained polymer composition was washed with water and acetone to obtain coated polymer particles having, on the surface, a hydrophilic polymer layer having a quaternary ammonium group. The obtained coated polymer particles were found to have an average particle size of 10 μm by measurement using a particle size distribution measurement apparatus (AccuSizer 780, manufactured by Particle Sizing Systems).

10 g of the obtained coated polymer particles was dispersed in 10.0 mL of ion exchange water to prepare pre-reaction slurry. Subsequently, 10 mL of N,N-dimethylaminopropylamine (manufactured by Wako Pure Chemical Industries, Ltd.) was added to this slurry with stirring, and the mixture was reacted at 70° C. for 4 hours. After the completion of the reaction, the supernatant was removed using a centrifuge (manufactured by Hitachi, Ltd., "Himac CR20G"), and the residue was washed with ion exchange water. After the washing, the supernatant was removed using a centrifuge. This washing with ion exchange water was further repeated four times to obtain a packing material for ion exchange chromatography having a quaternary ammonium group and a tertiary amino group on the surface of the substrate particles.

as a mixture of the primer corresponding to unmethylated DNA and the primer corresponding to methylated DNA at a molar ratio of 50:50. The PCR involved initial thermal denaturation at 95° C. for 5 minutes, followed by 45 cycles each involving 94° C. for 30 seconds→57° C. for 30 seconds→72° C. for 40 seconds, and subsequent elongation reaction at 72° C. for 10 minutes. After the completion of the PCR, 5 μL of the reaction solution was mixed with 1 μL of a loading dye solution, then applied to a 3% agarose gel supplemented with ethidium bromide, and electrophoresed to confirm that the PCR amplification product of interest was obtained. The positive control (100% methylated DNA) and the negative control (0% methylated DNA) used were commercially available control DNA (EPITECT(R) PCR control DNA, Qiagen N.V.). The sequences of the PCR amplification products of the 0% and 100% methylated DNAs and the sequence of each PCR primer are shown in Table 2.

TABLE 2

| Target gene name | Product size (bp) | Sequence |
|---|---|---|
| MLH1 Region DfCr 0% methylation | 99 | *TG* AACCAATAGGAAGAG*TG* GACAG*TG* ATCTCTAA*TG TG* CAAG*TG* CATATCCTTCTAGGTAG*TG* GGCAGTAGC*TG* CTT CAGGGAGGGA*TG* AAGAGACCCA (SEQ ID NO: 2) |
| MLH1 Region DfCr 100% methylation | 99 | *CG* AACCAATAGGAAGAG*CG* GACAG*CG* ATCTCTAA*CG CG* CAAG*CG* CATATCCTTCTAGGTAG*CG* GGCAGTAGC*CG* CTT CAGGGAGGGA*CG* AAGAGACCCA (SEQ ID NO: 3) |
| Primer Region DfCr (for Methylated DNA) | forward reverse | CGAATTAATAGGAAGAGCGGATAG (SEQ ID NO: 4) TAAATCTCTTCGTCCCTCCC (SEQ ID NO: 5) |
| Primer Region DfCr (for Unmethylated DNA) | forward reverse | TGAATTAATAGGAAGAGTGGATAG (SEQ ID NO: 6) TAAATCTCTTCATCCCTCCC (SEQ ID NO: 7) |

Primer-binding sites are underlined.
CpG sites are indicated in bold italic type.

A stainless column (column size: inside diameter 4.6 mm×length 20 mm) of a liquid chromatography system was packed with the packing material for ion exchange chromatography.

(2) Extraction and Bisulfite Treatment of Genomic DNA

The T specimen of each patient was treated using QIAamp DNA FFPE Tissue Kit (manufactured by Qiagen N.V.) to extract high-molecular-weight DNA. The N specimen of each patient was treated using QIAamp DNA Blood Maxi Kit (manufactured by Qiagen N.V.) to extract high-molecular-weight DNA. 500 ng of each DNA was treated with bisulfite using EpiTect Bisulfite Kits (manufactured by Qiagen N.V.).

(3) PCR

The bisulfite-treated genomic DNA obtained in the preceding step (2) was amplified by PCR. The amplification region was set to a 99-bp region (region DfCr) flanked by the PCR primers shown in Table 2, in the MLH1 promoter. The PCR was performed using a 25 μL of a reaction solution containing 10 ng of template DNA, GeneAmp 1×PCR buffer (manufactured by Life Technologies Corp.), 200 μmol/L GeneAmp dNTP Mix (manufactured by Life Technologies Corp.), 0.75 U AmpliTaq Gold DNA Polymerase (manufactured by Life Technologies Corp.), and 0.25 μmol/L forward and reverse primers. Since the primer-binding regions of the template DNA contained CpG sites, the primers were used (4) HPLC Analysis The anion exchange column prepared in (1) was used in ion exchange chromatography under the following conditions to separate and detect each PCR amplification product obtained in the preceding step (3).

System: LC-20A series (manufactured by Shimadzu Corp.)
Eluent: eluent A: 25 mmol/L tris-HCl buffer solution (pH 7.5)
    eluent B: 25 mmol/L tris-HCl buffer solution (pH 7.5)+1 mol/L ammonium sulfate
Analysis time: 15 min
Elution method: the mixing ratio of eluent B was linearly increased under the following gradient conditions:

0 min (40% eluent B)→10 min (100% eluent B)

Specimen: the PCR amplification product obtained in (2)
Flow rate: 1.0 mL/min
Detection wavelength: 260 nm
Sample injection volume: 5 μL
Column temperature: 70° C.

The DNA methylation rate was determined by establishing an association between the peak retention times of the positive control (100% methylated DNA) and the negative control (0% methylated DNA) and DNA methylation rates, and preparing a two-point calibration curve. An average retention time of the positive control and the negative control was calculated as the retention time (reference value) of DNA having a methylation rate of 50%. The DNA of each specimen was determined as "highly methylated DNA" when the peak retention time of the detection signal of the DNA was equal to or shorter than the reference value, and determined as "low methylated DNA" when the peak retention time of the detection signal of the DNA was longer than the reference value.

(5) Determination of Tissue Containing Colorectal Cancer on Basis of Chromatogram The HPLC chromatogram obtained from patient ID: S-1 is shown in FIG. 1. The HPLC chromatogram obtained from patient ID: S-2 is shown in FIG. 2. The HPLC chromatogram obtained from patient ID: S-3 is shown in FIG. 3. The HPLC chromatogram obtained from patient ID: S-4 is shown in FIG. 4.

The T specimen of patient ID: S-1 was a specimen in which one allele was highly methylated and the other allele was also highly methylated or lost due to LOH. It was therefore considered that a peak indicating a high methylation rate would be detected. In the N specimen, only one allele was methylated. It was therefore considered that both a peak indicating highly methylated DNA and a peak indicating unmethylated DNA would be detected. As a result of HPLC analysis, a peak was detected in the T specimen at almost the same elution time (around 4.08 minutes) as that of the positive control (100% methylated DNA). Peaks were respectively detected in the N specimen at an elution time (around 4.13 minutes) slightly longer than that of the positive control and at almost the same elution time (around 4.25 minutes) as that of the negative control (0% methylated DNA), and substantially a bimodal chromatogram was obtained. From these results, it was able to be confirmed by HPLC that: the DNA region of the T specimen was almost 100% methylated; and the DNA region of the N specimen was unmethylated or heterozygously highly methylated. Specifically, patient ID: S-1 can be determined as a patient without Lynch syndrome from the HPLC chromatogram of the T specimen. Also, patient ID: S-1 can be determined as a patient having hemimethylated DNA at least in the MLH1 region and suspected of being a constitutional epimutation case from the HPLC chromatogram of the N specimen.

The T specimen of patient ID: S-2 was a specimen having MSI-H in MSI examination and almost no methylation of MLH1. It was therefore considered that a peak indicating low methylated DNA would be detected. The N specimen also had almost no methylation of MLH1. It was therefore considered that a peak indicating low methylated DNA would be detected. As a result of HPLC analysis, a peak was detected in both the T specimen and the N specimen at almost the same elution time (around 4.28 minutes) as that of the negative control (0% methylated DNA). From these results, it was able to be confirmed by HPLC that the DNA regions of both the T specimen and the N specimen were low methylated. Specifically, patient ID: S-2 can be determined as likely to be a Lynch syndrome patient from the HPLC chromatogram of the T specimen.

The T specimen of patient ID: S-3 was a specimen having MSS in MSI examination and almost no methylation of MLH1. It was therefore considered that a peak indicating a low methylation rate would be detected. The N specimen also had almost no methylation of MLH1. It was therefore considered that a peak indicating low methylated DNA would be detected. As a result of HPLC analysis, a peak was detected in both the T specimen and the N specimen at almost the same elution time (around 4.25 minutes) as that of the negative control (0% methylated DNA). From these results, it was able to be confirmed by HPLC that the DNA regions of both the T specimen and the N specimen were low methylated. Specifically, patient ID: S-3 is determined as likely to be a Lynch syndrome patient from the HPLC chromatogram of the T specimen. However, patient ID: S-3 can be determined as a patient without Lynch syndrome by the combination of the HPLC chromatogram of the T specimen and MSI examination.

The T specimen of patient ID: S-4 was a specimen confirmed to have MSI-H in MSI examination, have the disappearance of MLH1 protein expression in immunohistochemical examination, and have highly methylated MLH1 promoter region in a pyrosequencer. It was therefore considered that a peak indicating a high methylation rate would be detected. The N specimen had almost no methylation of MLH1. It was therefore considered that a peak indicating low methylated DNA would be detected. As a result of HPLC analysis, a peak was detected in the T specimen at almost the same elution time (around 4.10 minutes) as that of the positive control (100% methylated DNA). A peak was detected in the N specimen at almost the same elution time (around 4.25 minutes) as that of the negative control (0% methylated DNA). From these results, it was able to be confirmed by HPLC that: the DNA region of the T specimen was almost 100% methylated; and the DNA region of the N specimen was low methylated. Specifically, patient ID: S-4 can be determined as a patient without Lynch syndrome from the HPLC chromatogram of the T specimen.

Reference Example 2

The specimens of the Lynch syndrome patient of patient ID: S-2 were studied for whether the methylation of different regions of the MLH1 gene promoter could be determined from HPLC chromatograms using primers different from those of Reference Example 1. The column used was the column of Reference Example 1(1). DNA was subjected to bisulfite treatment, PCR, and HPLC according to the procedures of Examples 1(2) to 1(4). In the PCR, five regions (regions A to E) were amplified as a portion of the MLH1 gene promoter region. DNA having a methylation rate of 0% (negative control) or 100% (positive control) in these PCR amplification regions was also analyzed by HPLC according to similar procedures. The sequences of the PCR amplification products of the 0% and 100% methylated DNAs are shown in Tables 3 and 4. The sequence of each PCR primer is shown in Table 5. Since the primer-binding regions of the template DNA as to the regions B to E contained CpG sites, the primers were used as a mixture of the primer corresponding to unmethylated DNA and the primer corresponding to methylated DNA at a molar ratio of 50:50.

TABLE 3

| Target gene name | Product size (bp) | Sequence |
|---|---|---|
| MLH1 Region A 0% methylation | 182 | CTCTTCAGGAGTGAAGGAGGCCA*TG* GGCAAGT*TG* CCCTGA *TG* CAGA*TG* CTCCACCAGGGC*TG* *TG* *TG* C*TG* C*TG* TC *TG* CCACATAC*TG* C*TG* TAGTAT*TG* TGCTCAGCCT*TG* TAGTGG*TG* CCTGA*TG* T*TG* *TG* TT*TG* *TG* GGTAGCTA*TG* |

TABLE 3-continued

| Target gene name | Product size (bp) | Sequence |
|---|---|---|
| | | ATGAGG*TG* *GTG* *ACAGACCAGGCACAGGGCCCCAT* (SEQ ID NO: 8) |
| MLH1 Region A 100% methylation | 182 | <u>CTCTTCAGGAGTGAAGGAGGC*CG* GGCAAGT*CG* CCCTGA *CG* CAGA*CG* CTCCACCAGGGC*CG* *CG* *CG* CT*CG* *CG* T*CG*</u> CCACATA*CG* CT*CG* TAGTATT*CG* TGCTCAGCCT*CG* T AGTG*CG* CCTGA*CG* T*CG* *CG* TT*CG* *CG* GGTAGCTA*CG* A TGAGG*CG* *GCG* *ACAGACCAGGCACAGGGCCCCAT* (SEQ ID NO: 9) |
| MLH1 Region b 0% methylation | 205 | <u>GACAGACCAGGCACAGGGCCCCAT*TG* CCCT*CTG* GAGGCTC</u> CACCACCAAATAA*TG* CTGGGTCCACT*TG* GG*CTG* GAAA ACTAGAGCCT*TG* T*TG* ACTTCCATCTTGCTTCTTTTGGG *TG* TCATCCACATTCT*GTG* GGAGGCCACAAGAGCAGGGCCA A*TG* TTAGAAAGGCTG CAAGGGGAGAGG<u>AGGAGCCTGAGAA G*TG* CCAAGCA</u> (SEQ ID NO: 10) |
| MLH1 Region B 100% methylation | 205 | <u>GACAGACCAGGCACAGGGCCCCAT*CG* CCCT*CCG* GAGGCTC</u> CACCACCAAATAA*CG* CTGGGTCCACT*CG* GG*CG* GAAAAC TAGAGCCT*CG* T*CG* ACTTCCATCTTGCTTCTTTTGGG *CG* TCATCCACATTCT*GCG* GGAGGCCACAAGAGCAGGGCCA A*CG* TTAGAAAGG*CG* CAAGGGGAGAGG<u>AGGAGCCTGAGAA G*CG* CCAAGCA</u> (SEQ ID NO: 11) |
| MLH1 Region C 0% methylation | 233 | <u>AGAGGAGGAGCCTGAGAAG*TG* CC</u>AAGCACCTCCTC*TG* CTC T*GTG* CCAGATCACCTCAGCAGAGGCACACAAGCC*TG* GTTC *TG* GCATCTCTGCTCCTATTGGCTGGATATTT*TG* TATTCCC *TG* AGCTCCTAAAAA*TG* AACCAATAGGAAGAG*TG* GACA*GTG* ATCTCTAA*TG* *TG* CAAG*TG* CATATCCTTCTAGGTAG*TG* GGCAGTAGC*TG* CTTC<u>AGGGAGGGA*TG* AAGAGACCCA</u> (SEQ ID NO: 12) |
| MLh1 Region C 100% methylation | 233 | <u>AGAGGAGGAGCCTGAGAAG*CG* CC</u>AGCACCTCCT*CCG* CTC T*GCG* CCAGATCACCTCAGCAGAGGCACACAAGCC*CG* GTTC *CG* GCATCTCTGCTCCTATTGGCTGGATATTT*CG* TATTCCC *CG* AGCTCCTAAAAA*CG*AACCAATAGGAAGAG*CG* GACA*GCG* ATCTCTAA*CG* *CG* CAAG*CG* CATATCCTTCTAGGTAG*CG* GGCAGTAGC*CG* CTTC<u>AGGGAGGGA*CG*AAGAGACCCA</u> (SEQ ID NO: 13) |

Primer-binding sites are underlined.
CpG sites are indicated in bold italic type.

TABLE 4

| Target gene name | Product size (bp) | Sequence |
|---|---|---|
| MLH1 Region D 0% methylation | 234 | *TG* <u>AACCAATAGGAAGAG*TG* GACA*GTG* ATCTCTAA*TG* *TG* CAAG*TG* CATATCCTTCTAGGTAG*TG* GGCAGTAGC*TG* CTT</u> CAGGGAGGGA*TG* AAGAGACCCAGCAACCCACAGAGTTGAGA AATTTGACTGGCATTCAAGCTGTCCAATCAATAGCTG*CTG* C TGAAGGGTGGGGCTGGATG*GTG* TAAGCTACAGCTGAAGGAA GAA*TG* TGAGCA*TG*AGGCACTGAGGTGATTGGCTGA (SEQ ID NO: 14) |
| MLH1 Region D 100% methylation | 234 | *CG* <u>AACCAATAGGAAGAG*CG* GACA*CG* ATCTCTAA*CG* *CG*C AAG*CG* CATATCCTTCTAGGTAG*CG* GGCAGTAGCCGCTTCA</u> GGGAGGGA*CG* AAGAGACCCAGCAACCCACAGAGTTGAGAAA TTTGACTGGCATTCAAGCTGTCCAATCAATAGCTG*CG* CTG AAGGGTGGGGCTGGATG*GCG* TAAGCTACAGCTGAAGGAAGA A*CG* TGAGCA*CG*AGGCACTGAGGTGATTGGCTGA (SEQ ID NO: 15) |
| MLH1 Region E 0% methylation | 159 | <u>GGCACTGAGGTGATTGGCTGAAGGCACTT*CTG* TTGAGCATC</u> TAGA*TG* TTTCCTTGGCTCTTCTG*GTG* CCAAAATG*TG* TT *TG* TGGCAGGGGTTA*TG* *GTG* GCTGGA*TG* AGACAGTGGT GAAC*TG* CAT*TG* *GTG* <u>GGGGAAGTTATCCAGTG GCCAG C</u> (SEQ ID NO: 16) |

TABLE 4-continued

| Target gene name | Product size (bp) | Sequence |
|---|---|---|
| MLH1 Region E 100% methylation | 159 | GGCACTGAGGTGATTGGCTGAAGGCACTTCCG TTGAGCATC TAGACG TTTCCTTGGCTCTTCTGGCG CCAAAATGTCG TT CG TGGCAGGGGTTATTCGCG GCTGGACG AGACAGTGGT GAACCG CATCG CG GCGGGGGAAGTTATCCAGCG GCCAGC (SEQ ID NO: 17) |

Primer-binding sites are underlined.
CpG sites are indicated in bold italic type.

TABLE 5

| Primer name | | Sequence |
|---|---|---|
| Primer Region A | forward | TTTTTTAGGAGTGAAGGAGG (SEQ ID NO: 18) |
| | reverse | ATAAAACCCTATACCTAATC TATC (SEQ ID NO: 19) |
| Primer Region B (for Methylated DNA) | forward | GATAGATTAGGTATAGGGTT TTAT (SEQ ID NO: 20) |
| | reverse | TACTTAACGCTTCTCAAACT CCT (SEQ ID NO: 21) |
| (for Unmethylated DNA) | forward | GATAGATTAGGTATAGGGTT TTAT (SEQ ID NO: 20) |
| | reverse | TACTTAACACTTCTCAAACT CCT (SEQ ID NO: 22) |
| Primer Region C (for Methylated DNA) | forward | AGAGGAGGAGTTTGAGAAGC GTT (SEQ ID NO: 23) |
| | reverse | TAAATCTCTTCGTCCCTCCC (SEQ ID NO: 24) |
| (for Unmethylated DNA) | forward | AGAGGAGGAGTTTGAGAAGT GTT (SEQ ID NO: 25) |
| | reverse | TAAATCTCTTCATCCCTCCC (SEQ ID NO: 26) |
| Primer Region D (for Methylated DNA) | forward | CGAATTAATAGGAAGAGCGG ATAG (SEQ ID NO: 27) |
| | reverse | TCAACCAATCACCTCAATAC C (SEQ ID NO: 28) |
| (for Unmethylated DNA) | forward | TGAATTAATAGGAAGAGTGG ATAG (SEQ ID NO: 29) |
| | reverse | TCAACCAATCACCTCAATAC C (SEQ ID NO: 28) |
| Primer Region E (for Methylated DNA) | forward | GGTATTGAGGTGATTGGTTG A (SEQ ID NO: 30) |
| | reverse | ACTAACCGCTAAATAACTTC CCC (SEQ ID NO: 31) |
| (for Unmethylated DNA) | forward | GGTATTGAGGTGATTGGTTG A (SEQ ID NO: 30) |
| | reverse | ACTAACCACTAAATAACTTC CCC (SEQ ID NO: 32) |

The HPLC chromatogram as to the region A is shown in FIG. 5. The HPLC chromatogram as to the region B is shown in FIG. 6. The HPLC chromatogram as to the region C is shown in FIG. 7. The HPLC chromatogram as to the region D is shown in FIG. 8. The HPLC chromatogram as to the region E is shown in FIG. 9. As shown in FIGS. 5 to 9, a peak indicating low methylated DNA was obtained from the T specimen for all the regions A to E. Specifically, patient ID: S-2 was also able to be determined as likely to have Lynch syndrome by examining the DNA methylation of any of the regions A, B, C, D, and E in the MLH1 promoter region represented by SEQ ID NO: 1. These results demonstrated that a patient likely to have Lynch syndrome can be determined by determining the methylation status of one or more CpG sites in the MLH1 promoter region in the T specimen of the patient on the basis of a HPLC chromatogram.

The present Examples demonstrated that the methylation of the MLH1 promoter region can be measured by use of chromatography analysis to thereby highly accurately differentiate between patients with Lynch syndrome and patients without Lynch syndrome. Conventional methylation analysis by pyrosequencing requires several days. By contrast, in the method of the present invention, Lynch syndrome can be screened for rapidly and easily because a chromatogram is obtained in approximately 10 minutes. The method of the present invention is useful in differential diagnosis for denying the possibility of Lynch syndrome in patients suspected of having Lynch syndrome by conventional MSI examination or the like, but manifesting no abnormality in MLH1 in genetic examination.

The invention claimed is:

1. A method for determining if a subject with a tumor has Lynch syndrome, comprising:
   (1) obtaining a tissue or cell sample from the tumor;
   (2) analyzing the tissue or cell sample to determine if:
      a. the tumor has no mutation in MLH1 in genetic examination and at least one of the properties selected from the group consisting of:
         i. MSI-H in an MSI examination;
         ii. no expression of MLH-1 in the tumor determined by immunohistochemical examination; and
         iii. a reduced expression of MLH-1 in the tumor determined by immunohistochemical examination;
   (3) treating genomic DNA prepared from the tissue or cell sample having no mutation in MLH1 and at least one of the properties (2)(a) (i), (ii), and (iii) with bisulfite;
   (4) amplifying by PCR, using at least one primer selected from the group consisting of primers consisting of the nucleotide sequences represented by SEQ ID Nos. 4 to 7 and 20 to 32, DNA comprising a portion or the whole of MLH1 promoter region from the bisulfite-treated DNA obtained in (3);
   (5) subjecting the PCR amplification product obtained in (4) to ion exchange chromatography to obtain a detection signal;
   (6) determining whether or not the peak of the detection signal obtained in (5) is a peak indicating highly methylated DNA; and
   (7) determining the tumor as a tumor derived from a subject without Lynch syndrome when the peak is determined as a peak indicating highly methylated DNA in (6).

2. The method according to claim 1, wherein the tumor is a tumor in the large intestine, the endometrium, the stomach, the ovarium, the small intestine, the bile duct, the pancreas, the renal pelvis, the urinary duct, the brain, or the sebaceous gland.

3. The method according to claim 1, wherein, in (4), the DNA comprising a portion or the whole of MLH1 promoter region further comprises a portion or the whole of intron 1 region.

4. The method according to claim 1, wherein the ion exchange chromatography is anion exchange chromatography.

5. The method according to claim 1, wherein column packing material in the ion exchange chromatography has both a strong cationic group and a weak cationic group on the surface.

6. A method for obtaining data for determining if a subject with a tumor has Lynch syndrome, comprising:
   (1) obtaining a tissue or cell sample from the tumor;
   (2) analyzing the tissue or cell sample to determine if:
      a. the tumor has no mutation in MLH1 in genetic examination and at least one of the properties selected from the group consisting of:
         i. MSI-H in an MSI examination;
         ii. no expression of MLH-1 in the tumor determined by immunohistochemical examination; and
         iii. a reduced expression of MLH-1 in the tumor determined by immunohistochemical examination;
   (3) treating genomic DNA prepared from the tissue sample having no mutation in MLH1 and at least one of the properties (2)(a)(i), (ii), and (iii) with bisulfite;
   (4) amplifying, by PCR, using at least one primer selected from the group consisting of primers consisting of the nucleotide sequences represented by SEQ ID Nos. 4 to 7 and 20 to 32, DNA comprising a portion or the whole of MLH1 promoter region from the bisulfate-treated DNA obtained in (3);
   (5) subjecting the PCR amplification product obtained in (4) to ion exchange chromatography to obtain a detection signal; and
   (6) determining whether the peak of the detection signal obtained in (5) is a peak indicating highly methylated DNA wherein a peak indicating highly methylated DNA indicates the tumor is a tumor derived from a subject without Lynch syndrome or a peak not indicating highly methylated DNA.

7. The method according to claim 6, wherein the tumor is a tumor in the large intestine, the endometrium, the stomach, the ovarium, the small intestine, the bile duct, the pancreas, the renal pelvis, the urinary duct, the brain, or the sebaceous gland.

8. The method according to claim 6, wherein in (4), the DNA comprising a portion or the whole of MLH1 promoter region further comprises a portion or the whole of intron 1 region.

9. The method according to claim 6, wherein the ion exchange chromatography is anion exchange chromatography.

10. The method according to claim 6, wherein column packing material in the ion exchange chromatography has both a strong cationic group and a weak cationic group on the surface.

11. The method according to claim 1, wherein, in (4), the PCR is performed by using at least one set of primers selected from the group consisting of a set of primers consisting of the nucleotide sequences represented by SEQ ID NOs: 4, 5, 6, and 7, a set of primers consisting of the nucleotide sequences represented by SEQ ID NOs: 20, 21, and 22, a set of primers consisting of the nucleotide sequences represented by SEQ ID NOs: 23, 24, 25, and 26, a set of primers consisting of the nucleotide sequences represented by SEQ ID NOs: 27, 28, and 29, and a set of primers consisting of the nucleotide sequences represented by SEQ ID NOs: 30, 31, and 32.

12. The method according to claim 6, wherein, in (4), the PCR is performed by using at least one primer selected from the group consisting of primers consisting of the nucleotide sequences represented by SEQ ID NOs: 4 to 7.

13. The method according to claim 6, wherein, in (4), the PCR is performed by using at least one set of primers selected from the group consisting of a set of primers consisting of the nucleotide sequences represented by SEQ ID NOs: 4, 5, 6, and 7, a set of primers consisting of the nucleotide sequences represented by SEQ ID NOs: 20, 21, and 22, a set of primers consisting of the nucleotide sequences represented by SEQ ID NOs: 23, 24, 25, and 26, a set of primers consisting of the nucleotide sequences represented by SEQ ID NOs: 27, 28, and 29, and a set of primers consisting of the nucleotide sequences represented by SEQ ID NOs: 30, 31, and 32.

* * * * *

SEQUENCE LISTING

<160> NUMBER OF SEQ ID NOS: 33

<210> SEQ ID NO 1
<211> LENGTH: 855
<212> TYPE: DNA
<213> ORGANISM: Homo sapiens

<400> SEQUENCE: 1
ctcttcagga gtgaaggagg ccacgggcaa gtcgccctga cgcagacgct ccaccagggc    60
cgcgcgctcg ccgtccgcca cataccgctc gtagtattcg tgctcagcct cgtagtggcg   120
cctgacgtcg cgttcgcggg tagctacgat gaggcggcga cagaccaggc acagggcccc   180

```
atcgccctcc ggaggctcca ccaccaaata acgctgggtc cactcgggcc ggaaaactag        240
agcctcgtcg acttccatct tgcttctttt gggcgtcatc cacattctgc gggaggccac        300
aagagcaggg ccaacgttag aaaggccgca aggggagagg aggagcctga aagcgccaa         360 gcacctcctc cgctctgcgc cagatcacct cagcagaggc acacaagccc ggttccggca        420
tctctgctcc tattggctgg atatttcgta ttccccgagc tcctaaaaac gaaccaatag        480
gaagagcgga cagcgatctc taacgcgcaa gcgcatatcc ttctaggtag cgggcagtag        540
ccgcttcagg gagggacgaa gagacccagc aacccacaga gttgagaaat ttgactggca        600
ttcaagctgt ccaatcaata gctgccgctg aagggtgggg ctggatggcg taagctacag        660
ctgaaggaag aacgtgagca cgaggcactg aggtgattgg ctgaaggcac ttccgttgag        720
catctagacg tttccttggc tcttctggcg ccaaaatgtc gttcgtggca ggggttattc        780
ggcggctgga cgagacagtg gtgaaccgca tcgcggcggg ggaagttatc cagcggccag        840
ctaatgctat caaag                                                         855

<210> SEQ ID NO 2
<211> LENGTH: 99
<212> TYPE: DNA
<213> ORGANISM: Homo sapiens

<400> SEQUENCE: 2
tgaaccaata ggaagagtgg acagtgatct ctaatgtgca agtgcatatc cttctaggta         60
gtgggcagta gctgcttcag ggagggatga agagaccca                                99

<210> SEQ ID NO 3
<211> LENGTH: 99
<212> TYPE: DNA
<213> ORGANISM: Homo sapiens

<400> SEQUENCE: 3
cgaaccaata ggaagagcgg acagcgatct ctaacgcgca agcgcatatc cttctaggta         60
gcgggcagta gccgcttcag ggagggacga agagaccca                                99

<210> SEQ ID NO 4
<211> LENGTH: 24
<212> TYPE: DNA
<213> ORGANISM: Artificial
<220> FEATURE:
<223> OTHER INFORMATION: Synthesized primer sequence

<400> SEQUENCE: 4
cgaattaata ggaagagcgg atag                                                24

<210> SEQ ID NO 5
<211> LENGTH: 20
<212> TYPE: DNA
<213> ORGANISM: Artificial
<220> FEATURE:
<223> OTHER INFORMATION: Synthesized primer sequence

<400> SEQUENCE: 5
taaatctctt cgtccctccc                                                     20

<210> SEQ ID NO 6
<211> LENGTH: 24
<212> TYPE: DNA
<213> ORGANISM: Artificial
<220> FEATURE:
<223> OTHER INFORMATION: Synthesized primer sequence
```

```
<400> SEQUENCE: 6
tgaattaata ggaagagtgg atag                                              24

<210> SEQ ID NO 7
<211> LENGTH: 20
<212> TYPE: DNA
<213> ORGANISM: Artificial
<220> FEATURE:
<223> OTHER INFORMATION: Synthesized primer sequence

<400> SEQUENCE: 7
taaatctctt catccctccc                                                   20

<210> SEQ ID NO 8
<211> LENGTH: 182
<212> TYPE: DNA
<213> ORGANISM: Homo sapiens

<400> SEQUENCE: 8
ctcttcagga gtgaaggagg ccatgggcaa gttgccctga tgcagatgct ccaccagggc       60
tgtgtgcttg ctgtctgcca catactgctt gtagtatttg tgctcagcct tgtagtggtg      120
cctgatgttg tgtttgtggg tagctatgat gaggtggtga cagaccaggc acagggcccc      180
at                                                                     182

<210> SEQ ID NO 9
<211> LENGTH: 182
<212> TYPE: DNA
<213> ORGANISM: Homo sapiens

<400> SEQUENCE: 9
ctcttcagga gtgaaggagg ccacgggcaa gtcgccctga cgcagacgct ccaccagggc       60
cgcgcgctcg ccgtccgcca cataccgctc gtagtattcg tgctcagcct cgtagtggcg      120
cctgacgtcg cgttcgcggg tagctacgat gaggcggcga cagaccaggc acagggcccc      180
at                                                                     182

<210> SEQ ID NO 10
<211> LENGTH: 205
<212> TYPE: DNA
<213> ORGANISM: Homo sapiens

<400> SEQUENCE: 10
gacagaccag gcacagggcc ccattgccct ctggaggctc caccaccaaa taatgctggg       60
tccacttggg ctggaaaact agagccttgt tgacttccat cttgcttctt ttgggtgtca      120
tccacattct gtgggaggcc acaagagcag ggccaatgtt agaaaggctg caaggggaga      180
ggaggagcct gagaagtgcc aagca                                            205

<210> SEQ ID NO 11
<211> LENGTH: 205
<212> TYPE: DNA
<213> ORGANISM: Homo sapiens

<400> SEQUENCE: 11
gacagaccag gcacagggcc ccatcgccct ccggaggctc caccaccaaa taacgctggg       60
tccactcggg ccggaaaact agagcctcgt cgacttccat cttgcttctt ttgggcgtca      120
tccacattct gcgggaggcc acaagagcag ggccaacgtt agaaaggccg caaggggaga      180
```
ggaggagcct gagaagcgcc aagca                                              205

<210> SEQ ID NO 12
<211> LENGTH: 233
<212> TYPE: DNA
<213> ORGANISM: Homo sapiens

<400> SEQUENCE: 12
agaggaggag cctgagaagt gccaagcacc tcctctgctc tgtgccagat cacctcagca        60
gaggcacaca agcctggttc tggcatctct gctcctattg gctggatatt ttgtattccc       120
tgagctccta aaaatgaacc aataggaaga gtggacagtg atctctaatg tgcaagtgca       180
tatccttcta ggtagtgggc agtagctgct tcagggaggg atgaagagac cca              233

<210> SEQ ID NO 13
<211> LENGTH: 233
<212> TYPE: DNA
<213> ORGANISM: Homo sapiens

<400> SEQUENCE: 13
agaggaggag cctgagaagc gccaagcacc tcctccgctc tgcgccagat cacctcagca        60
gaggcacaca agcccggttc cggcatctct gctcctattg gctggatatt tcgtattccc       120
cgagctccta aaacgaacc aataggaaga gcggacagcg atctctaacg cgcaagcgca        180
tatccttcta ggtagcgggc agtagccgct tcagggaggg acgaagagac cca              233

<210> SEQ ID NO 14
<211> LENGTH: 235
<212> TYPE: DNA
<213> ORGANISM: Homo sapiens

<400> SEQUENCE: 14
tgaaccaata ggaagagtgg acagtgatct ctaatgtgca agtgcatatc cttctaggta        60
gtgggcagta gctgcttcag ggagggatga agagacccag caaccacag agttgagaaa       120 tttgactggc attcaagctg tccaatcaat agctgctgct gaagggtggg gctggatggt       180
gtaagctaca gctgaaggaa gaatgtgagc atgaggcact gaggtgattg ctga             235

<210> SEQ ID NO 15
<211> LENGTH: 235
<212> TYPE: DNA
<213> ORGANISM: Homo sapiens

<400> SEQUENCE: 15
cgaaccaata ggaagagcgg acagcgatct ctaacgcgca agcgcatatc cttctaggta        60
gcgggcagta gccgcttcag ggagggacga agagacccag caaccacag agttgagaaa       120 tttgactggc attcaagctg tccaatcaat agctgccgct gaagggtggg gctggatggc       180
gtaagctaca gctgaaggaa gaacgtgagc acgaggcact gaggtgattg ctga             235

<210> SEQ ID NO 16
<211> LENGTH: 158
<212> TYPE: DNA
<213> ORGANISM: Homo sapiens

<400> SEQUENCE: 16
ggcactgagg tgattggctg aaggcacttc tgttgagcat ctagatgttt ccttggctct        60
tctggtgcca aaatgttgtt tgtggcaggg gttatttggt ggctggatga gacagtggtg       120
aactgcattg tggtggggga agttatccag tggccagc                               158

<210> SEQ ID NO 17
<211> LENGTH: 158
<212> TYPE: DNA
<213> ORGANISM: Homo sapiens

<400> SEQUENCE: 17
ggcactgagg tgattggctg aaggcacttc cgttgagcat ctagacgttt ccttggctct    60
tctggcgcca aaatgtcgtt cgtggcaggg gttattcggc ggctggacga gacagtggtg   120
aaccgcatcg cggcggggga agttatccag cggccagc                           158

<210> SEQ ID NO 18
<211> LENGTH: 20
<212> TYPE: DNA
<213> ORGANISM: Artificial
<220> FEATURE:
<223> OTHER INFORMATION: Synthesized primer sequence

<400> SEQUENCE: 18 tttttttagga gtgaaggagg                                               20

<210> SEQ ID NO 19
<211> LENGTH: 24
<212> TYPE: DNA
<213> ORGANISM: Artificial
<220> FEATURE:
<223> OTHER INFORMATION: Synthesized primer sequence

<400> SEQUENCE: 19
ataaaaccct atacctaatc tatc                                           24

<210> SEQ ID NO 20
<211> LENGTH: 24
<212> TYPE: DNA
<213> ORGANISM: Artificial
<220> FEATURE:
<223> OTHER INFORMATION: Synthesized primer sequence

<400> SEQUENCE: 20
gatagattag gtatagggtt ttat                                           24

<210> SEQ ID NO 21
<211> LENGTH: 23
<212> TYPE: DNA
<213> ORGANISM: Artificial
<220> FEATURE:
<223> OTHER INFORMATION: Synthesized primer sequence

<400> SEQUENCE: 21
tacttaacgc ttctcaaact cct                                            23

<210> SEQ ID NO 22
<211> LENGTH: 23
<212> TYPE: DNA
<213> ORGANISM: Artificial
<220> FEATURE:
<223> OTHER INFORMATION: Synthesized primer sequence

<400> SEQUENCE: 22
tacttaacac ttctcaaact cct                                            23

<210> SEQ ID NO 23
<211> LENGTH: 23
<212> TYPE: DNA

```
<213> ORGANISM: Artificial
<220> FEATURE:
<223> OTHER INFORMATION: Synthesized primer sequence

<400> SEQUENCE: 23
agaggaggag tttgagaagc gtt                                           23

<210> SEQ ID NO 24
<211> LENGTH: 20
<212> TYPE: DNA
<213> ORGANISM: Artificial
<220> FEATURE:
<223> OTHER INFORMATION: Synthesized primer sequence

<400> SEQUENCE: 24
taaatctctt cgtccctccc                                               20

<210> SEQ ID NO 25
<211> LENGTH: 23
<212> TYPE: DNA
<213> ORGANISM: Artificial
<220> FEATURE:
<223> OTHER INFORMATION: Synthesized primer sequence

<400> SEQUENCE: 25
agaggaggag tttgagaagt gtt                                           23

<210> SEQ ID NO 26
<211> LENGTH: 20
<212> TYPE: DNA
<213> ORGANISM: Artificial
<220> FEATURE:
<223> OTHER INFORMATION: Synthesized primer sequence

<400> SEQUENCE: 26
taaatctctt catccctccc                                               20

<210> SEQ ID NO 27
<211> LENGTH: 24
<212> TYPE: DNA
<213> ORGANISM: Artificial
<220> FEATURE:
<223> OTHER INFORMATION: Synthesized primer sequence

<400> SEQUENCE: 27
cgaattaata ggaagagcgg atag                                          24

<210> SEQ ID NO 28
<211> LENGTH: 21
<212> TYPE: DNA
<213> ORGANISM: Artificial
<220> FEATURE:
<223> OTHER INFORMATION: Synthesized primer sequence

<400> SEQUENCE: 28
tcaaccaatc acctcaatac c                                             21

<210> SEQ ID NO 29
<211> LENGTH: 24
<212> TYPE: DNA
<213> ORGANISM: Artificial
<220> FEATURE:
<223> OTHER INFORMATION: Synthesized primer sequence

<400> SEQUENCE: 29
tgaattaata ggaagagtgg atag                                          24
```

<210> SEQ ID NO 30
<211> LENGTH: 21
<212> TYPE: DNA
<213> ORGANISM: Artificial
<220> FEATURE:
<223> OTHER INFORMATION: Synthesized primer sequence

<400> SEQUENCE: 30
ggtattgagg tgattggttg a                                             21

<210> SEQ ID NO 31
<211> LENGTH: 23
<212> TYPE: DNA
<213> ORGANISM: Artificial
<220> FEATURE:
<223> OTHER INFORMATION: Synthesized primer sequence

<400> SEQUENCE: 31
actaaccgct aaataacttc ccc                                           23

<210> SEQ ID NO 32
<211> LENGTH: 23
<212> TYPE: DNA
<213> ORGANISM: Artificial
<220> FEATURE:
<223> OTHER INFORMATION: Synthesized primer sequence

<400> SEQUENCE: 32
actaaccact aaataacttc ccc                                           23

<210> SEQ ID NO 33
<211> LENGTH: 2955
<212> TYPE: DNA
<213> ORGANISM: Homo sapiens
<220> FEATURE:
<223> OTHER INFORMATION: MLH1 Intron 1

<400> SEQUENCE: 33
gtacggaggg agtcgagccg ggctcactta agggctacga cttaacgggc cgcgtcactc    60
aatggcgcgg acacgcctct tgcccgggc agaggcatgt acagcgcatg cccacaacgg   120
cggaggccgc cgggttccct gacgtgccag tcaggccttc tccttttccg cagaccgtgt   180
gtttctttac cgctctcccc cgagaccttt taagggttgt ttggagtgta agtggaggaa   240
tatacgtagt gttgtcttaa tggtaccgtt aactaagtaa ggaagccact taatttaaaa   300
ttatgtatgc agaacatgcg aagttaaaag atgtataaaa gcttaagatg gggagaaaaa   360
ccttttttca gagggtactg tgttactgtt ttcttgcttt tcattcattc cagaaatcat   420
ctgttcacat ccaaaggcac aattcatttt gagtttcttt caaacaaat cgtttgtagt   480 tttaggacag gctgatgcac tttgggcttg acttctgatt accctattgt taaattagtg   540 accctctta gtgttttcct gtcctttatt tcggaggacg cacttcgaag ataccagatt   600
ttatgggtca tccttggatt tgaagctta taactgtgac aaaaaatgtg aagggaagag   660
atttgaaaca tgtggaagga aaagtgagtg cagactataa acttccaaaa agacaagccc   720
aaaatacacc taaacgttat gtcagattat tttgttaaaa tcagttgtta gtgacgtccg   780
tacgttaata gaaaaagaa tgcttcagtt tggagtggta ggtttctaga gggatttatt   840
gtgaaagtat aaactattca ggcaatgggg actgagagaa cagtgggtag aaaggaccac   900
tgaaggaaag gaagagaatt ggaaggtaga tgaaagaagg agcaagaacc tgggatgtt   960

```
ttttcctttt cacttgtaat agtagtaaca gaagcaatgg cagactggct tttgtttcta    1020
ctgtgttaga atgaattgac aggacaactg ggcctattat tgtactgtgc cagaatactg    1080
taaaacaaaa ctaaacatac tagcttggtg gcttgtaatt aattacttaa gtggagattt    1140 ttatttttt ttatttttt ttttagacgg agtctcactt tgtcacccag gctggagtgc      1200
agtggcgcga tctcagctga ctgcaacctc ctcctcacag gttcaaggga gattctcctg    1260
cctcagcctc ccgagtagct aggactatag gcatgtgcca ccacacctgg ctaattttgt    1320 attttagta gagatgggat ttctccatgt tggtcaggct ggtgtcaaaa ctctcgatct     1380
caggtgaacc gcctgcctca gccttccaaa gtgctgggat tacaggcgtg agccaccgcg    1440
ccctgcagtt ttttgtattt taatagaga cagggtttca ccatgttagc caggatggtc     1500
tcgatttcct gacctcaggt gatctgcccg ctttggcctc ccaaagtgct gggattacaa    1560
gcatgagcca ccgcgcccgg ctcaagtgga gattttata tggagtccag ttatactctt     1620
tttaatatat aagttgagat gactaataca acttcaatac aggggctcat gagaaatgtc    1680
tgtaatattt aagtaactta ttgtcttctt tcttttttt ttaagatgaa gtcttactct     1740
gttgcccagg cggaagtgca gtggcgtgat cttggctcag gcaacctct gcctcctggt     1800 ttcaagcgat cttcctgcct cagcctcccg agtagctggg agtacaggcg tgcatgacca    1860
cacccggcta atttttttat ttttagtaga cgggggtttt ctccatgttg gccgggctgg    1920
tcttgaactc ctgacctcag gtgatccgcc cacctcagcc tccccaagtg ttgggattac    1980
aggtgtgagc ccccgtgccc agcctattat cttatttctg aataaagaat tgtctgtgtg    2040
gggaatagat aactctttct catgcagccc ctgctagaaa atttgttttc tctagcagtt    2100
ggtctgtgct tataggctac tctttgaaag cacaaaaaat ttattgactt cttttttttg    2160
ggtttttttt tttttttgag acagagtttt gcccttgttg cccaggttgg agtgcaatgg    2220
cgcgatctca gctcaccgca acctccacct cctgggttca agtgattctc ctgccttagc    2280
ctcctgagta gctgggatta caggcatgcg tcaccatgcc tggctaattt tgtattttta   2340
gtacaaatgg ggtttctcca tgttggtcag gctggtctca aactcctgac ctcaggtgat    2400
ccacccgcct tggcctccca aagtgctggg attatgggtg tgagccattg cgcctggcca    2460
gaaaattcat tgacttccta agatttatt aactttctgc attactttt tttttcccct     2520 ccatcgtaaa tataaaggg aatagtagag aaaatcattc agaatttat ttttttagtga    2580 cattatttag tgacatttta ttagagtcac ttaggaacct gaggctgaat aaagttcagg    2640
taaaagtaaa attagttgag aagagacatc tgccaaaaga aatctatttt taacttcact    2700
tgctgtcttt cctagaggaa cagaaatagt gctgaatgtc ctattagaaa tgatggttgc    2760
tctgcccgtc tcttccctct ctctcacaca atatgtaaac tcatacagtg tatgagcctg    2820
taagacaaag gaaaacacg ttaatgaggc actattgttt gtatttggag tttgttatca     2880
ttgcttggct catattaaaa tatgtacatt agagtagttg cagactgata aattattttc    2940
tgtttgattt gccag                                                     2955
```